United States Patent
Zheng

(10) Patent No.: US 9,546,360 B2
(45) Date of Patent: Jan. 17, 2017

(54) GAIN-OF-FUNCTION ADAMTS13 VARIANTS RESISTANT TO AUTO ANTIBODY INHIBITION AND METHODS OF USE THEREOF

(71) Applicant: The Children's Hospital of Philadelphia, Philadelphia, PA (US)

(72) Inventor: X. Long Zheng, Wallingford, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 0 days.

(21) Appl. No.: 14/312,041

(22) Filed: Jun. 23, 2014

(65) Prior Publication Data
US 2015/0044171 A1 Feb. 12, 2015

Related U.S. Application Data

(63) Continuation-in-part of application No. PCT/US2012/071289, filed on Dec. 21, 2012.

(60) Provisional application No. 61/734,580, filed on Dec. 7, 2012, provisional application No. 61/731,193, filed on Nov. 29, 2012, provisional application No. 61/578,295, filed on Dec. 21, 2011.

(51) Int. Cl.
| | |
|---|---|
| A61K 38/16 | (2006.01) |
| A61K 38/00 | (2006.01) |
| C12P 21/06 | (2006.01) |
| C12N 1/22 | (2006.01) |
| C12N 9/50 | (2006.01) |
| C12N 9/64 | (2006.01) |
| A61K 38/48 | (2006.01) |
| A61K 48/00 | (2006.01) |

(52) U.S. Cl.
CPC ......... *C12N 9/6489* (2013.01); *A61K 38/4886* (2013.01); *C12Y 304/24087* (2013.01); *A61K 48/00* (2013.01)

(58) Field of Classification Search
USPC ............ 514/21.2, 15.3; 435/69.1, 252.3, 219
See application file for complete search history.

(56) References Cited

U.S. PATENT DOCUMENTS

2012/0064057 A1* 3/2012 Soejima ............. A61K 38/4886 424/94.6

FOREIGN PATENT DOCUMENTS

JP WO 2009/001743 * 12/2008

OTHER PUBLICATIONS

Kokame et al Mutations and common polymorphisms in ADAMTS13 gene responsible for von Willebrand factor-cleaving protease activity 11902-11907 _PNAS _Sep. 3, 2002 _vol. 99 _No. 18.*

Jian et al Gain-of-functionADAMTS13 variants that are resistant to autoantibodies against ADAMTS13 in patients with acquired thrombotic thrombocytopenic purpura Blood, Apr. 19, 2012 _vol. 119, No. 16 3836-3843.*

Ngo, in The Protein Folding Problem and Tertiary Structure Prediction, Merz et al. (eds.), Birkhauser Boston: Boston, MA, pp. 433 and 492-495, 1994.*

Voet, Biochemistry John Wiley and Sons, 1990, pp. 126-128.*

Kimchi-Sarfaty C et al., A "silent" polymorphism in the MDR1 gene changes substrate specificity.Science. Jan. 26, 2007;315(5811

(56) References Cited

OTHER PUBLICATIONS

Cataland et al., Cyclosporine and plasma exchange in thrombotic thrombocytopenic purpura: long-term follow-up with serial analysis of ADAMTS13 activity, Br J Haematol, 2007, 486-93, 139.
Cataland et al., An evaluation of cyclosporine alone for the treatment of early recurrences of thombotic thrombocytopenic purpura, J Thromb Haemost, 2006, 1162-4, 4.
Zheng et al., Pathogenesis of Thrombotic Microangiopathies, Annu. Rev.Path.Mech.Dis., 2008, 249-277, 3.
Soejima et al., ADAMTS-13 cysteine-rich/spacer domains are functionally essential for von Willebrand factor cleavage, Blood, 2003, 3232-7, 102.
Pos et al., An autoantibody epitope comprising residues R660, Y661, and Y665 in the ADAMTS13 spacer domain identifies a binding site for the A2 domain of VWF, Blood, 2010, 1640-1649, 115.
Al et al., The proximal carboxyl-terminal domains of ADAMTS13 determine substrate specificity and are all required for cleavage of von Willebrand factor, J Biol Chem, 2005, 29428-34, 280.
Gao et al., Exosite interactions contribute to tension-induced cleavage of von Willebrand factor by the antithrombotic ADAMTS13 metalloprotease, Proc Natl Acad Sci U S A, 2006, 19099-04, 103.
Gao et al., Extensive contacts between ADAMTS13 exosites and von Willebrand factor domain A2 contribute to substrate specificity, Blood, 2008, 1713-1719, 112.
Zheng et al., Cleavage of von Willebrand factor requires the spacer domain of the metalloprotease ADAMTS13, J Biol Chem, 2003, 30136-41, 278.
Zhou et al., Enzymatically active ADAMTS13 variants are not inhibited by anti-ADAMTS13 autoantibodies: a novel therapeutic strategy? J Biol Chem, 2005, 39934-39941, 280.
Raife et al., Leukocyte proteases cleave von Willebrand factor at or near the ADAMTS13 cleavage site, Blood, 2009, 1666-74, 114.
Zhang et al., Creation of a recombinant peptide substrate for fluorescence resonance energy transfer-based protease assays, Anal. Biochem., 2006, 298-300, 358.
Cao et al., Factor VIII accelerates proteolytic cleavage of von Willebrand factor by ADAMTS13, Proc Natl Acad Sci USA, 2008, 7416-21, 105.
Jin et al., Amino acid residues Arg(659), Arg(660), and Tyr(661) in the spacer domain of ADAMTS13 are critical for cleavage of von Willebrand factor, Blood, 2010, 2300-2310, 115.
Akiyama et al., Crystal structures of the noncatalytic domains of ADAMTS13 reveal multiple discontinuous exosites for von Willebrand factor, Proc Natl Acad Sci USA, 2009, 19274-19279, 106.
Zhang et al., Structural specializations of A2, a force-sensing domain in the ultralarge vascular protein von Willebrand factor, Proc.Natl.Acad.Sci.U.S.A, 2009, 9226-9231, 106.
Klaus et al., Epitope mapping of ADAMTS13 autoantibodies in acquired thrombotic thrombocytopenic purpura, Blood, 2004, 4514-9, 103.
George et al., How I treat patients with thrombotic thrombocytopenic purpura: 2010, Blood, 2010, 4060-4069, 116.
Zheng et al., Effect of plasma exchange on plasma ADAMTS13 metalloprotease activity, inhibitor level, and clinical outcome in patients with idiopathic and non-idiopathic thrombotic thrombocytopenic purpura, Blood, 2004, 4043-9, 103.

* cited by examiner

| Residues | Domain | # unique peptides | Hydrogens exchanged with scFV 4-20: w/o scFV 4-20 |
|---|---|---|---|
| 28-228 | M | 25 | 1.3 |
| 229-428 | M/D/T | 7 | 1.4 |
| 429-628 | T/C/S | 10 | 0.9 |
| 629-642 | S | 6 | 0.4† |
| 643-685 | S | 10 | 1.0 |

Figure 11A

629 RVALTEDRLPRLEE 642

■ Less than 0.4
□ Between 0.4 and 0.7
■ Greater than 0.8

Figure 11B

Survival rates in mice expressing control and inhibitory scFV after being challenged with Shigatoxin

Figure 15

GAIN-OF-FUNCTION ADAMTS13 VARIANTS RESISTANT TO AUTO ANTIBODY INHIBITION AND METHODS OF USE THEREOF

This application is continuation-in-part of PCT/US2012/71289 filed Dec. 21, 2012 which in turn claims priority to U.S. Provisional Application Nos. 61/578,295, 61/731,193 and 61/734,580 filed Dec. 21, 2011, Nov. 29, 2012 and Dec. 7, 2012 respectively. Each of the foregoing applications is incorporated herein by reference.

Pursuant to 35 U.S.C. §202(c) it is acknowledged that the U.S. Government has rights in the invention described, which was made in part with funds from the National Institutes of Health, Grant Number, HL074124.

FIELD OF THE INVENTION

This invention relates to the fields of physiology and hematology. More specifically, the invention provides gain-of-function ADAMTS13 variants which are resistant to autoantibody inhibition and therefore useful for the treatment of aberrant thrombus formation such as that observed in TTP, myocardial infarction, and stroke.

BACKGROUND OF THE INVENTION

Several publications and patent documents are cited throughout the specification in order to describe the state of the art to which this invention pertains. Each of these citations is incorporated herein by reference as though set forth in full.

ADAMTS13 (A Disintegrin And Metalloprotease with ThromboSpondin type1 repeats-13) cleaves ultra large (UL) von Willebrand factor (VWF) on endothelial cells[1] and soluble VWF in the flowing blood[2,3] or at site of injury where VWF-rich platelet thrombi are formed[4-6]. This cleavage is highly specific occurring at the $Tyr^{1605}$-$Met^{1606}$ bond in the A2 domain[7]. In vivo, fluid shear stress accelerates the cleavage of cell bound ULVWF[1,8] and soluble VWF in circulation[2,3]. In vitro addition of a denaturant such as urea[9] or guanidine[7] markedly accelerates the cleavage of soluble VWF by ADAMTS13. These findings facilitate the development of various biochemical assays for assessing ADAMTS13 activity.

The importance of VWF proteolysis is highlighted by the development of a fatal syndrome thrombotic thrombocytopenic purpura (TTP) when plasma ADAMTS13 activity is severely deficient, either due to hereditary mutations of ADAMTS13 gene[10] or acquired formation of autoantibodies that inhibit ADAMTS13 activity[11-13]. Nearly all adult patients with severely deficient ADAMTS13 activity harbor polyclonal immunoglobulin Gs (IgGs) that bind the Cys-rich and spacer domains, particularly the spacer domain of ADAMTS13[13-17]. Recent studies have shown that exosite 3 (i.e. Y659-Y665) and several other adjacent amino acid residues (i.e. R568 and F592) in the spacer domain comprise a major antigenic epitope for autoantibodies in TTP[18,19]. This region is also found to play an essential role in proteolytic cleavage of VWF under various conditions[6,20-24] and inhibition of arterial thrombus formation in vivo[6].

Clearly a need exists for the identification of those residues in the ADAMTS13 spacer region which modulate substrate recognition and autoantibody recognition. This information should provide guidance for the development of therapeutic compositions useful for the treatment of TTP, myocardial infarction and stroke, and other inflammatory and arterial thrombotic disorders.

SUMMARY OF THE INVENTION

In accordance with the present invention, isolated gain of function ADAMTS13 variants are provided comprising at least one amino acid change in the spacer domain of ADAMTS13, provided the change is not an alanine substitution. The variants of the invention retain proteolytic activity and exhibit resistance to autoantibody inhibition. In a preferred embodiment, the variant is one of the M1 variant, the M2 variant, the M3 variant, the M4 variant or the M5 variant. In a particularly preferred embodiment, the variants are the M4 and M5 variants.

Also encompassed by the present invention is a pharmaceutical composition comprising the isolated ADAMTS13 variants described above in a biologically acceptable carrier including platelets, nanoparticles, and adeno-associate viral vectors, etc.

In yet another aspect, the invention provides a method for the treatment of TTP. An exemplary method comprises administration of an effective amount of the purified recombinant ADAMTS13 variants or delivered through platelets, nanoparticles, and AAV, etc., described above to a patient need thereof, the ADAMTS13 variants inhibiting thrombus formation in the patient. In a particularly preferred embodiment, the variant exhibits increased proteolytic activity when compared to wild type ADAMTS13 and/or is resistant to TTP patient autoantibody inhibition.

BRIEF DESCRIPTION OF THE DRAWINGS

FIG. 1. Western blot and proteolytic activity of ADAMTS13 and mutants.

FIG. 2A. Schematic domain organization of full-length ADAMTS13 (top), surface representation of exosite 3 and adjacent residues in the spacer domain of ADAMTS13 (Left), and names of various ADAMTS13 variants with amino acid substitution (Right). FIG. 2B. Western blotting with anti-V5 detects recombinant WT and variants in the conditioned medium (50 nM each lane). Arrowhead indicates full-length ADAMTS13 of ~195 kDa with little degradation. FIG. 2C. Relative specific proteolytic activity of the variants in comparison to WT is shown. The results are the mean and SD of three independent experiments (n=3). **P<0.001 is considered to be statically highly significant.

FIG. 3A. Human plasma-derived VWF (150 nM) pre-denatured with 1.5 M urea was mixed with WT, M1, M2, M3, M4, and M5 (0.04 nM and 0.2 nM) in the absence or in the presence of EDTA (10 mM) (last lane) and dialyzed against 10 mM Tris-HCl, pH 8.0 containing 1.5 M urea at 37° for 4 h. The cleavage of VWF was determined by agarose (1%) gel electrophoresis and Western blotting with rabbit anti-VWF IgG (1:5,000), followed by IRDye 800CW-labeled goat anti-rabbit IgG (1:10,000). FIG. 3B. The relative activity was determined by ImageJ quantitation of the ratio of cleavage product (P, arrowhead) to high molecular weight (HMW) VWF multimers in each sample. The specific activity was normalized to that of WT (1 arbitrary unit). The results are the means±standard error of the mean from three independent experiments.

FIG. 7A. Surface representation of ADAMTS13-DTCS fragment; FIG. 7B. Close-up view of the hydrophobic cluster in the exosite of ADAMTS1-spacer domain. This pocket contains a cluster of hydrophobic residues (L591, F592, L637, P638, L668, T669, and ring of Y661 and Y665), lined by basic residues (R568, R589, R636, and R660) supported by 8 β sheets (i.e. β1, 2, 3, 6, 7, 8, 9, and 10). FIG. 7C. A substitution of these surface residues with those in yellow appears to increase hydrophobicity of this pocket. FIG. 7D. VWF-A2 (1653-1668) forms an amphipathic helix (α6). Here shown are the hydrophobic residues facing to the top and charged residues to the bottom. This amphipathic helix may govern specificity to the ADAMTS13-spacer exosite by inserting its hydrophobic side into the pocket.

FIG. 8A) ADAMTS13 domains. M=metalloprotease, D=disintegrin, TSP=thrombospondin type-1, C=cysteine-rich, s=spacer, CUB=CUB. FIG. 8B) Crystal structure of ADAMTS13 DTCS with surfaces is shown with domains colored according to FIG. 9A. Exosites 3 and 4 are boxed. The spacer domain is enlarged showing exosites are solvent-exposed. FIG. 8C) Residues of exosites 3 and 4 create a solvent-exposed interface for substrate and/or antibody binding.

FIG. 9.

FIG. 10A) Multimer analysis of wild type ADAMTS13 and deletion ADAMTS13 mutants. FIG. 10B) Multimer analysis of motif B mutations. All multimers are done with 150 nM VWF, denatured in 1.5 M urea for 4 hours at 37° C. in the presence of ADAMTS13. EDTA (20 mM) was included in B lane 1 as control.

FIG. 11. FIG. 11A) Results of hydrogen exchange for ADAMTS13 MDTCS construct. Exchange was done at pH 7.3 and stopped at 0° C. The only statistically significant difference in exchange was observed between residues 629 and 642 in the spacer domain, shown by the dagger (†). FIG. 11B) The region containing motif B shows the least exchange in the presence of scFV 4-20. 6 unique peptides exist and are shown below the sequence. One peptide is not shown because data obtained was incomplete.

FIG. 12A) Schematic representation of whole IgG and a single chain fragment of the variable region (scFVs) of human monoclonal antibody against ADAMTS13 isolated from an acquired TTP patient from B-cells through phage display library screening. FIG. 12B) Inhibition of plasma ADAMTS13 activity by affinity purified scFV 4-20 expressed in E. coli using a VWF-73 FRETS assay. Concentration-dependent inhibition of plasma ADAMTS13 is shown with an IC50 of 0.01 ug/ml.

FIG. 15. A graph showing survival rates in mice expressing control and inhibitory scFV after being challenged with shigatoxin-2. Clearly, mortality rate is significantly higher in the mice expressing inhibitory scFV4-20 than in mice expressing a control non-inhibitory scFV.

(FIG. 18A) shows the representative time-lapse images of thrombus formed within 10 min in Adamts13$^{-/-}$, transgenic, and wild type mice. (FIG. 18B) shows the quantification of fluorescence intensity over time (or the rate of thrombus formation) in the mesenteric arterioles of KO, transgenic (TG) and WT mice after being injured with 105 FeCl$_3$ using NIS image analysis software. The data were the mean and standard deviation from experiments on 3-5 mice in each group. Clearly, platelet-delivered ADAMTS13 significantly inhibits arterial thrombosis after injury.

FIG. 19A and FIG. 19B show the distribution of megakaryocyte ploidy after in vitro culturing of bone marrow derived megakaryocytes isolated from Adamts13$^{-/-}$ (FIG. 19A) and transgenic (FIG. 19B) mice in the presence of thrombopoietin. FIG. 19C represents the means and standard deviation of the ploidy distribution from 4 independent experiments. There was no statistical difference in the DNA content between KO and TG mice at various maturation stages. FIG. 19D-FIG. 19F are representative aggregation tracings of the washed platelets isolated from wild-type (WT), Adamts13$^{-/-}$ (KO) and transgenic (TG) mice after addition of collagen (2 ug/mL) (FIG. 19D), alpha-thrombin (0.1 U/mL) (FIG. 19E), and 2 MesADP (30 nM) (FIG. 19F) as indicated.

FIG. 21A. Schematic representation of animal protocol used to induce acquired ADAMTS13 deficiency and times for CBC analysis in WT and transgenic mice. FIG. 21B and FIG. 21C show the platelet counts in transgenic/scFv4-20 (closed dots) and wild type/scFv4-20 (open dots) mice prior to (pre) and 24 hours (D1) after being challenged with 5 and 10 micrograms per gram body weight of mVWF, respectively. FIG. 21D is mortality rate in transgenic/scFv4-20 and WT/ScFv4-20 mice after being challenged with mVWF. ANOVA used to determine the statistical significance of the differences among various groups. **indicates p value less than 0.01. FIG. 21E shows the histological analysis of the major organs obtained from WT mice/ScFv4-20 that died of high-dose mVWF challenge.

(FIG. 22A) The schematic diagram of AAV constructs. As shown, full-length murine ADAMTS13 protein consists of a signal peptide (S), prodomain (P), a metalloprotease domain (M), a disintegrin domain (D), the first thrombospondin type 1 repeat, a Cys-rich (C), and spacer domain (S) (ie, mdtcs). More distal C-terminus of murine ADAMTS13 contains an additional 7 thrombospondin type 1 repeats (2-8) and CUB domains (for complement C1r/C1s, Uegf, Bmp1). The fragment (approximately 2.4 kb) encoding amino acid residues 1 to 2055 of murine ADAMTS13, a hAAT promoter, and a bovine growth hormone polyadenylation signal (BGHpolyA) were cloned into an AAV vector (hAAT-mdtcs). The expression cassette was flanked by 2 inverted terminal repeats (ITR). In addition, a lacZ gene and a hAAT promoter were inserted into the same vector as a control (hAAT-lacZ). (FIG. 22B) The purified recombinant vectors, AAV8-hAAT-mdtcs (lane 1) and AAV8-hAATlacZ (lane 2), were revealed by Coomassie blue staining. Only 3 viral envelope proteins (VP1, VP2, and VP3) were detected in the final preparations, with the VP3 as the predominant band. Two asterisks indicate 2 minor contaminated proteins or degradation products in lane 1. (FIG. 22C) The amplification of murine ADAMTS13 fragment (approximately 0.25 kb, closed arrowheads) and beta-actin (approximately 0.5 kb, open arrowheads) mRNA in the brain, lung, heart, liver, spleen, and kidneys in mice treated with AAV8-hAAT-mdtcs (2.6×11 vg/kg) or AAV8-hAAT-lacZ or PBS, as indicated in the figure. The therapeutic transgene product was detected only in the liver of Adamts13$^{-/-}$ mice treated with AAV8-hAAT-mdtcs but not in the controls. (FIG. 22D-FIG. 22E) The positive (arrowheads) and negative staining with anti-murine ADAMTS13 IgG in the hepatocytes 2 weeks after intravenous administration (2.6×11 vg/kg) of AAV8-hAAT-mdtcs and AAV8-hAAT-lacZ, respectively. The staining was performed on the frozen sections after being fixed with ethanol/acetic acid (9/1) for 10 minutes at 220° C. An AlexaFluor568 donkey anti-rabbit IgG (Invitrogen) was used (1:500) for detection (red).

(FIG. 23A-FIG. 23B) The dynamic changes of plasma VWF-cleaving activity (U/mL) and antigen (mg/mL) over time (weeks), as determined by rFRETS-mVWF73 and ELISA, respectively, in mice treated with various doses of AAV8-hAAT-mdtcs. Each time point represents the mean 6 standard deviations (SD) of 5 individual mice (n=5). Wild-type murine plasma pooled from 10 mice was used as a standard for the calibration of proteolytic activity (1 U/mL). A purified recombinant mdtcs fragment spiked into the Adamts13$^{-/-}$ murine plasma was used for calibration of plasma antigen levels. (FIG. 23C-FIG. 23F) The daily platelet counts before (day 0) and after the Stx2 challenge in Adamts13$^{-/-}$ mice that were pretreated with a single dose of AAV8-hAAT-lacZ (1.3×12 vg/kg) or various doses of AAV8-hAAT-mdtcs as indicated. (FIG. 23G) The Kaplan-Meier survival rates over 7 days in mice treated with control vector and therapeutic AAV8 vector at various doses and challenged with Stx2. A P value, 0.001 is considered statistically significant.

DETAILED DESCRIPTION OF THE INVENTION

Figures 1A, 1B:
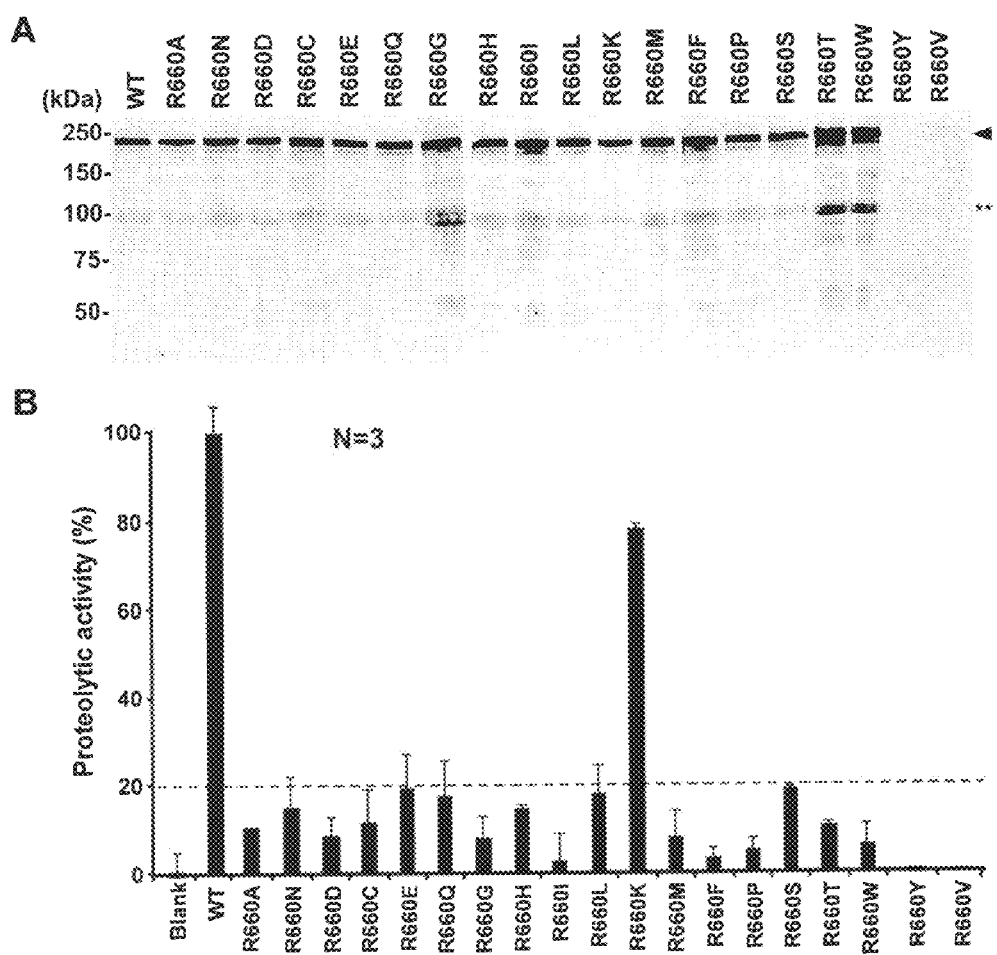
FIG. 1A. Western blotting with mouse anti-V5 IgG detects wild type ADAMTS13 (WT) and single point mutants at position 660 in the concentrated condition medium (~50 nM per lane). Arrowhead and double stars indicate the intact full-length ADAMTS13, ~195 kDa, and degradation product, respectively.
FIG. 1B. Relative proteolytic activity (%) of WT and single point variants assessed by the cleavage of rF-VWF73 as described in the Materials and Methods. Means and standard deviations from three independent experiments are shown (n=3). All mutants except for R660K have activity below 20% of WT.

Thrombotic thrombocytopenic purpura (TTP) is primarily caused by immunoglobulin G (IgG) autoantibodies against ADAMTS13. Nearly all TTP patients harbor IgGs that bind the spacer domain of ADAMTS13, a region critical for recognition and proteolysis of von Willebrand factor (VWF). We show that a modification of an exosite in the spacer domain generates ADAMTS13 variants with reduced autoantibody binding and preserved or enhanced specific activity. Site-directed mutagenesis was used to generate a series of ADAMTS13 variants and their functional properties were assessed. Of 24 novel variants, two (i.e. M4, R660K/F592Y/R568K/Y661F and M5, R660K/F592Y/R568K/Y661F/Y665F) exhibited increased specific activity by ~4-5 and ~10-12 fold to cleave peptide VWF73 and multimeric VWF, respectively. More interestingly, the gain-of-function ADAMTS13 variants were more resistant to inhibition by anti-ADAMTS13 autoantibodies from patients with acquired TTP, owing to reduced binding by anti-ADAMTS13 IgGs. Other variants are disclosed that possess alterations in the exosite 4. These results shed more light on the critical role of the exosite in the spacer domain in substrate recognition. Our findings also help understand the pathogenesis of autoimmune TTP. The autoantibody-resistant variants provide new agents for therapy of acquired TTP with inhibitors.

Another aspect of the invention relates to the treatment of stroke and other blood coagulation disorders. Data have shown that low ADAMTS13 activity is a risk factor for myocardial infraction and ischemic stroke. Indeed, recombinant ADAMTS13 is being tested in a phase I clinical trial for these disorders in addition to assessing efficacy for the treatment of TTP. The variants disclosed herein would also be suitable for this purpose. Thus, ADAMTS13 variants may be administered to a patient via infusion in a biologically compatible carrier. The polypeptides of the invention may optionally be encapsulated in to liposomes or other phospholipids to increase stability of the molecule. The polypeptides or complexes there of may be administered alone or in combination with other agents known to modulate thrombotic events. An appropriate composition in which to deliver ADAMTS13 can be determined by a medical practitioner upon consideration of a variety of physiological variables, including, but not limited to, the patient's condition and hemodynamic state. A variety of compositions well suited for different applications and routes of administration are well known in the art and described hereinbelow.

The preparation containing the purified polypeptide variant contains a physiologically acceptable matrix and is preferably formulated as a pharmaceutical preparation. The preparation can be formulated using substantially known prior art methods, it can be mixed with a buffer containing salts, such as NaCl, CaCl$_2$, and amino acids, such as glycine and/or lysine, and in a pH range from 6 to 8. Until needed, the purified preparation containing the polypeptides can be stored in the form of a finished solution or in lyophilized or deep-frozen form. Preferably the preparation is stored in lyophilized form and is dissolved into a visually clear solution using an appropriate reconstitution solution.

Alternatively, the preparation according to the present invention can also be made available as a liquid preparation or as a liquid that is deep-frozen.

The preparation according to the present invention is especially stable, i.e., it can be allowed to stand in dissolved form for a prolonged time prior to application. The preparation according to the present invention can be made available as a pharmaceutical preparation with anti thrombotic activity in the form of a one-component preparation or in combination with other factors in the form of a multi-component preparation.

Prior to processing the purified proteins into a pharmaceutical preparation, the purified proteins are subjected to the conventional quality controls and fashioned into a therapeutic form of presentation. In particular, during the recombinant manufacture, the purified preparation is tested for the absence of components from any cellular components (e.g., nucleic acids, cellular debris) possibly present during the purification process.

Another feature of this invention relates to making available a preparation which contains ADAMTS13 variants which is free from inactive intermediates and autoproteolytic degradation products.

The pharmaceutical preparation may contain dosages of between 10-1000 μg/kg, more preferably between about 10-250 μg/kg and most preferably between 10 and 75 μg/kg, with 40 μg/kg of the polypeptides being particularly preferred. Patients may be treated immediately upon presentation at the clinic with a coagulation disorder or thrombotic disorder. Alternatively, patients may receive a bolus infusion every one to three hours, or if sufficient improvement is observed, a once daily infusion of the polypeptides described herein.

DEFINITIONS

Various terms relating to the biological molecules of the present invention are used hereinabove and also throughout the specification and claims.

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it originates. For example, the "isolated nucleic acid" may comprise a DNA or cDNA molecule inserted into a vector, such as a plasmid or virus vector, or integrated into the DNA of a prokaryote or eukaryote.

With respect to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

The term "promoter region" refers to the transcriptional regulatory regions of a gene, which may be found at the 5' or 3' side of the coding region, or within the coding region, or within introns.

The term "vector" refers to a small carrier DNA molecule into which a DNA sequence can be inserted for introduction into a host cell where it will be replicated. An "expression vector" is a specialized vector that contains a gene or nucleic acid sequence with the necessary regulatory regions needed for expression in a host cell.

The term "operably linked" means that the regulatory sequences necessary for expression of a coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The term "substantially pure" refers to a preparation comprising at least 50-60% by weight the compound of interest (e.g., nucleic acid, oligonucleotide, protein, etc.). More preferably, the preparation comprises at least 75% by weight, and most preferably 90-99% by weight, of the compound of interest. Purity is measured by methods appropriate for the compound of interest (e.g. chromatographic methods, agarose or polyacrylamide gel electrophoresis, HPLC analysis, and the like).

The phrase "consisting essentially of" when referring to a particular nucleotide sequence or amino acid sequence means a sequence having the properties of a given SEQ ID NO:. For example, when used in reference to an amino acid sequence, the phrase includes the sequence per se and molecular modifications that would not affect the basic and novel characteristics of the sequence.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application for which the oligonucleotide is used.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and method of use. For example, for diagnostic applications, depending on the complexity of the target sequence, the oligonucleotide probe typically contains 15-25 or more nucleotides, although it may contain fewer nucleotides.

The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to act functionally as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product.

The primer may vary in length depending on the particular conditions and requirements of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

The term "percent identical" is used herein with reference to comparisons among nucleic acid or amino acid sequences. Nucleic acid and amino acid sequences are often compared using computer programs that align sequences of nucleic or amino acids thus defining the differences between the two. For purposes of this invention comparisons of nucleic acid sequences are performed using the GCG Wisconsin Package version 9.1, available from the Genetics Computer Group in Madison, Wis. For convenience, the default parameters (gap creation penalty=12, gap extension penalty=4) specified by that program are intended for use herein to compare sequence identity. Alternately, the Blastn 2.0 program provided by the National Center for Biotechnology Information (found on the world wide web at ncbi.nlm.nih.gov/blast/; Altschul et al., 1990, J Mol Biol 215:403-410) using a gapped alignment with default parameters, may be used to determine the level of identity and similarity between nucleic acid sequences and amino acid sequences.

The following materials and methods are provided to facilitate the practice of the present invention.

Constructs:

QuickChange site-directed mutagenesis regents (Stratagene) were used to replace one or a clustered of surface charged amino acid residues (R660, F592, R568, Y661, and Y665) in the β9-β10 variable region of the spacer domain. A pcDNA3.1 vector containing wild-type ADAMTS13-V5-His was used as a plate. The resulting variants with a desired mutation or mutations were sequenced to confirm the accuracy at the Nucleic Acid Core Facility, The Children's Hospital of Philadelphia.

Preparations of Recombinant ADAMTS13 and Variants:

COS7 and HEK-293 cells were transfected with plasmid and polyethylenimine (PEI) according to the manufacture instruction (CellNTech Advanced Cell System). Serum-free conditioned medium was collected 4 days after transfection and concentrated 50-100× using a filtration column (Millipore) in the presence of protease inhibitor cocktail (Sigma).

ELISA:

The concentrations of ADAMTS13 and variants in the concentrated conditioned medium were determined by a Sandwich enzyme-linked immunoassay (ELISA). Briefly, a high binding microtiter plate (NUNC) was coated with 100 µl of monoclonal anti-Disintegrin IgG (40 µg/ml) (Custom made in Green Mountain Antibody, Vermont, N.H.) overnight. The remaining binding sites were blocked for 30 min with 150 µl/well of 2.5% BSA in PBS. WT and variants diluted with PBS were added and incubated for 2 hours. After being washed with PBS, monoclonal anti-V5-HRP IgG (1:1,000) was added for detection. Previously purified WT was used as a calibration. All quantifications were repeated three times for consistency.

Western Blot:

The integrity of WT and variants in the concentrated conditioned medium were assessed by Western blotting after fractionation on 8% SDS-polyacrylamide gel under reduced conditions. After being transferred to a nitrocellulose membrane, recombinant WT and variants were blotted by anti-V5 IgG (1:5,000) and IRdye800CW-labeled goat anti-mouse IgG (1:20,000) (LI-COR, Lincoln) in 20 mM Tris-HCl, 150 mM NaCl containing 0.05% Tween20 and 1% casein (TB-STc). The fluorescent signal obtained with Odyssey imaging system (LI-COR, Lincoln, Nebr.) was converted to gray images.

Proteolytic Cleavage of VWF73 Peptide:

Maleimide-fluorescein-labeled VWF73 (rF-VWF73) (2 µM) as described previously[25;26] was incubated with ADAMTS13 and variants (0.2 nM) in 5 mM Bis-Tris, pH 6.0 containing 25 mM $CaCl_2$ and 0.005% Tween 20 in a 96-well white plate (Corning, N.Y.). The rate of fluorescence generation was monitored at 37° C. with a fluorescent microtiter plate reader (Molecular Devices, Sunnyvale, Calif.) (Ex/Em 485/535 nm) every minute for 30 min. Pooled normal human plasma was used as a reference.

Proteolytic Cleavage of Multimeric VWF Under Denaturing Conditions:

Purified plasma VWF (150 nM) was incubated with ADAMTS13 and variants in the conditioned medium (0.2 nM and 0.04 nM) or purified WT and variants (2 nM and 10 nM) at 37° C. for 4 hours on a membrane (0.25 µm, pore size) floating over 50 ml buffer (10 mM Tris-HCl, pH 8.0 containing 1.5 M urea in a conical tube. The digested material was withdrawn and denatured with sample buffer (70 mM Tris-HCl, pH6.5, 2.4% SDS, 0.67 M urea, and 4 mM EDTA) at 60° C. for 20 minutes. The denatured VWF was fractionated with 1% (wt/vol) SeaKem HGT agarose (Cambrex, East Rutherford, N.J.) gel. The protein was then transferred onto a nitrocellulose membrane and detected by Western blotting with anti-VWF IgG (1:5,000) and IRDye 800CW-labeled goat anti-rabbit IgG (1:10,000) (LI-COR Bioscience, Lincoln, Nebr.) as described previously[6;27].

Inhibition of Cleavage of VWF by Autoantibodies from TTP Patients:

Recombinant ADAMTS13 and variants (0.2 nM) were incubated with human monoclonal antibody against ADAMTS13-spacer domain isolated from a patient with idiopathic TTP (mAb II-1) (kindly provided by Dr. Jan Vorberg, Sanquin-AMC Landsteiner Laboratory, Amsterdam, the Netherlands) or with heat-inactivated (56° C. for 60 min) normal human plasma or patient plasmas (2.5-10 µl) in PBS for 30 min. The residual proteolytic activity was determined by cleavage of VWF multimers using agarose gel electrophoresis and Western blotting as described previously[6;27]. The percentage of inhibition was determined by comparing the residual activity in WT and variants after addition of control plasma with that after patient plasma.

Binding of Patient Anti-ADAMTS13 IgGs to ADAMTS13 and Variants:

An immunoprecipitation plus Western blotting analysis was used to detect the antigen and antibody reaction in solution as described previously[13]. WT and variants (50 ng) were incubated 5-10 µl of normal human plasma or patient plasma and 30 µl of protein A/G Sepharose 4B (Invitrogen) in 50 mM Tris-HCl, pH 7.6 containing 0.15 M NaCl, 1% bovine serum albumin (BSA), 1% Triton X-100, and 0.1% Tween-20 (TEST) at 4° C., overnight. After wash with TBST, the bound recombinant ADAMTS13 and variants were eluted from the beads and determined by Western blotting with anti-V5 IgG (1:5,000) (Invitrogen). The amount of bound primary antibody was determined by IRDye 800CW-labeled goat anti-mouse IgG (1:20,000) (LI-COR Bioscience, Lincoln, Nebr.) in TEST containing 1% casein as previously described[13].

Model of ADAMTS13 and VWF Interaction:

The interaction between ADAMTS13-spacer domain and VWF-A2 was modeled using the HHPred server plugin in PyMol software available on the world wide web at .pymol-.org/. The supplemental materials were made with Adobe Photoshop CS software.

The following examples are provided to illustrate certain embodiments of the invention. They are not intended to limit the invention in any way.

Example I

Figure 1C:
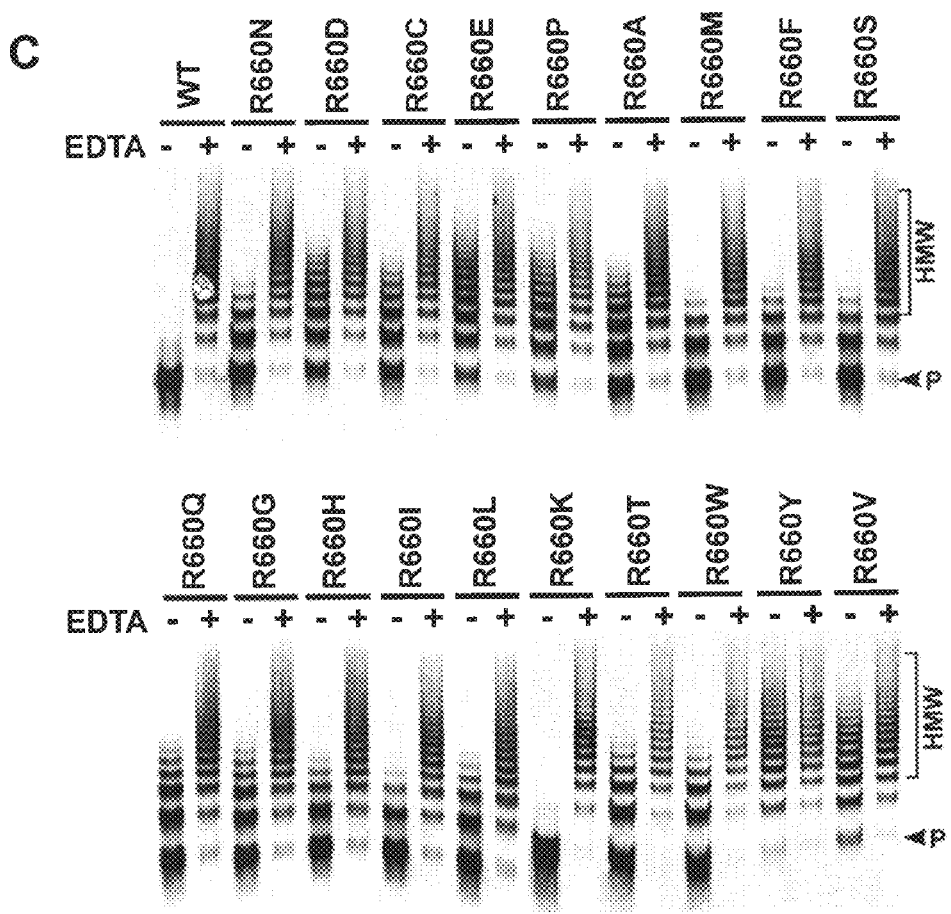
FIG. 1C. Proteolytic degradation of multimeric VWF by ADAMTS13 and single point mutants under denaturing conditions. Plasma-derived VWF (150 nM) was incubated with 0.2 nM of recombinant ADAMTS13 and mutants in the presence of 1.5 M urea for 4 hours. The proteolytic cleavage of VWF was determined by 1% agarose gel electrophoresis and Western blotting. The sign + or − indicates the presence or absence of 10 mM EDTA in the reaction. HMW and P indicate the high molecular weight multimers and cleavage product, respectively.

Gain-of-Function ADAMTS13 Variants that are Resistant to Inhibition by Anti-ADAMTS13 Autoantibodies from Patients with Acquired Idiopathic Thrombotic Thrombocytopenic Purpura Identification of the Optimal Residue at Position of 660 for ADAMTS13 Activity:

We and others have previously shown that R660 in the spacer domain of ADAMTS13 plays an essential role for substrate recognition (Genbank Accession No. mRNA, NM_139025.3; protein NM_6205941; Uniprot No. Q76XL8;[18;28]. A substitution of arginine at the position of 660 with alanine (R660A) nearly abolished proteolytic activity toward various substrates[18;28]. To determine the optimal residue at this position, we prepared a series of ADAMTS13 variants by replacing the R with 18 other amino acid residues. The resulting constructs were transiently expressed in COS-7 cells, which ran at ~195 kDa with little degradation on a SDS-polyacrylamide gel under reduced conditions (FIG. 1A). The specific activity was assessed by the cleavage of rF-VWF73 and VWF as described in the Methods. A replacement of R660 with any other residues except for K (M1, R660K) resulted in dramatically reduced cleavage of rF-VWF73 (FIG. 1B) and VWF (FIG. 1C). These results suggest that a positively charged residue such as arginine or lysine at position 660 in the spacer domain is required for ADAMTS13 activity.

Figure 2:
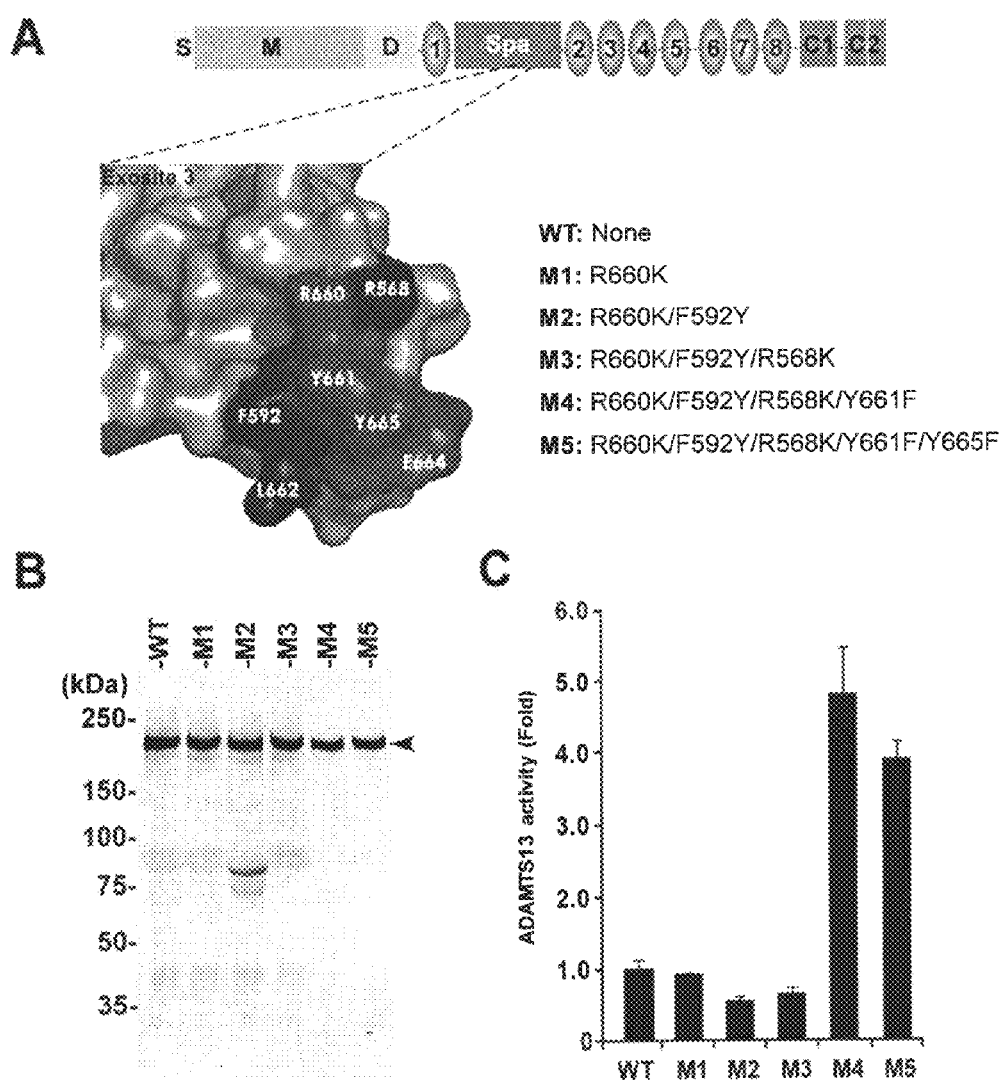
FIG. 2. Characterization of single and compound ADAMTS13 variants.
Figure 3:
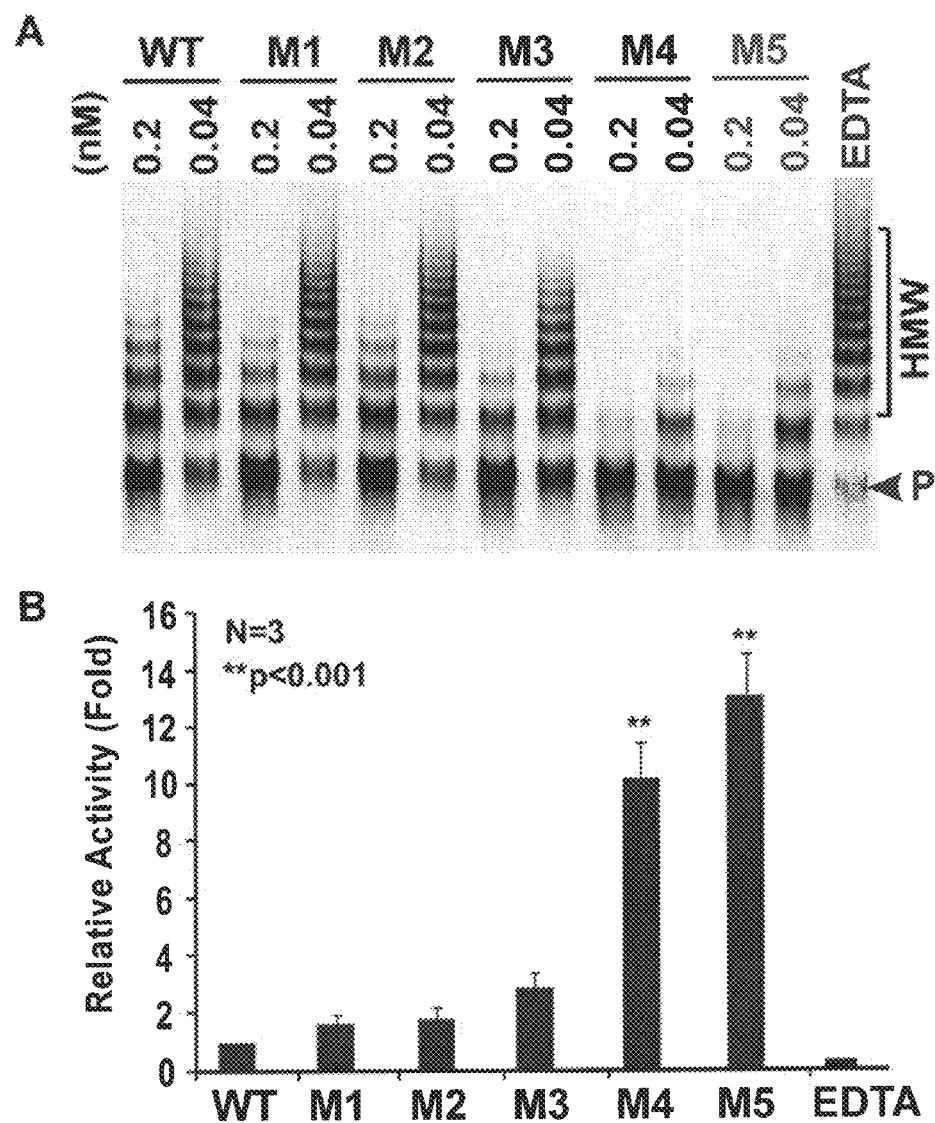
FIG. 3. Proteolytic cleavage of multimeric VWF by ADAMTS13 and variants under denaturing conditions.

Identification of Gain-of-Function ADAMTS13 Variants:

Based on the preliminary results described above, we performed additional site-directed mutagenesis experiments by sequentially replacing several other charged/hydrophobic residues on the surface loop in the spacer domain (i.e. R568, F592, R660, Y661, and Y665) with K, Y, F, and K, respectively (FIG. 2A). The resulting ADAMTS13 variants (i.e. M2, M3, M4, and M5) were also transiently in COST cells. All ran at ~195 kDa on SDS-polyacrylamide gel under reduced conditions (FIG. 2B). The specific activity was assessed by the cleavage of both rF-VWF73 and VWF. The variants M1, M2, and M3 exhibited similar activity to WT cleaving VWF73 peptide (FIG. 2C) and multimeric VWF (FIG. 3). However, the variants M4 and M5 exhibited increased specific activity by 4-5 fold (p<0.001) and 10-12 fold (p<0.001) in cleaving VWF73 peptide (FIG. 2C) and multimeric VWF (FIG. 3), respectively. These results demonstrate for the first time that gain-of-function ADAMTS13 variants can be engineered through a modification of exosite 3 in the spacer domain.

Identification of ADAMTS13 Variants Resistant to Autoantibodies in TTP Patients:

Exosite 3 plus several other adjacent residues in the spacer domain contains major binding sites for anti-ADAMTS13 autoantibodies in patients with acquired TTP[18;19]. We hypothesized that a modification in this region may alter the binding and inhibition of ADAMTS13 variants by patients' autoantibodies. To this aim, ADAMTS13 and variants (0.2 nM) were incubated for 60 min with a well-described human monoclonal antibody against spacer domain (mAb II-1) (35 µM) isolated from a patient with acquired TTP[6;14-16]. The mAb II-1 dramatically inhibited proteolytic activity of WT and M2, but not M1, M3, M4, and M5 (FIG. 4A), suggesting that R660 is critical for autoantibody inhibition. The reason why M1, but not M2 was resistant to inhibition is not clear.

When plasmas from TTP patients were used as the source of autoantibodies against ADAMTS13, proteolytic activity of WT, M1, and M2 was almost completely inhibited after 60 min of incubation (FIG. 4B, 4C, and Table 1), while variant M3 was only variably inhibited by the same amount of patient plasma, but variants M4 and M5 were resistant to patient plasma under the same conditions (FIG. 4B, 4C, and Table 1). These results indicate that the novel gain-of-function ADAMTS13 variants, especially M4 and M5, are more resistant to inhibition by both monoclonal and polyclonal anti-ADAMTS13 autoantibodies derived from patients with acquired idiopathic TTP.

Figure 4:
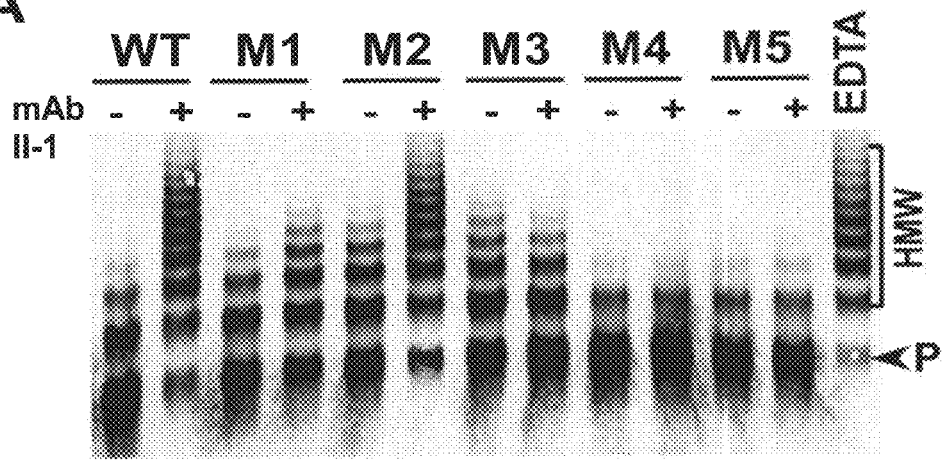
FIG. 4. Inhibition of proteolytic activity of WT-ADAMTS13 and ADAMTS13 variants by autoantibodies. Recombinant wild-type ADAMTS13 (WT) or ADAMTS13 variants (M1-M5) (final concentration of 0.2 nM) was incubated without (−) or with (+) 35 μM of human monoclonal anti-spacer IgG (mAb II-1) (FIG. 4A) or 5-10 μl of heat-inactivated normal human plasma (N) or TTP patient #1 plasma (P) (FIG. 4B) for 60 min. The residual activity was determined by the cleavage of pre-denatured multimeric VWF as described in the Materials and Methods. EDTA (10 mM) was included in the last lane as a negative control. The relative residual activity was determined by the ratio of product (P) to high molecular weight VWF (HMW) multimer using ImageJ and normalized to the activity in the presence of normal human plasma. The percentage of inhibition (means and standard deviation) by a panel of 12 TTP patient plasmas is shown in panel FIG. 4C. **p<0.001 indicates statistically highly significant difference between WT and three variants (M3, M4, and M5).
Figure 4:
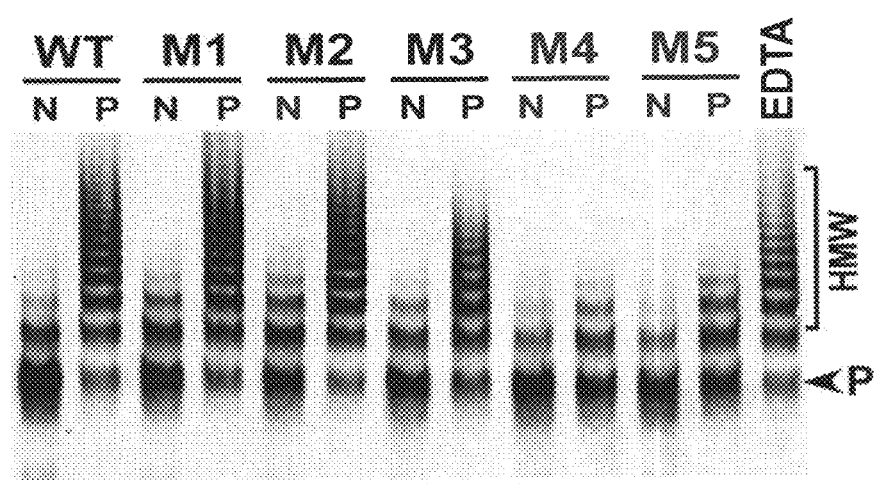
Figure 4:
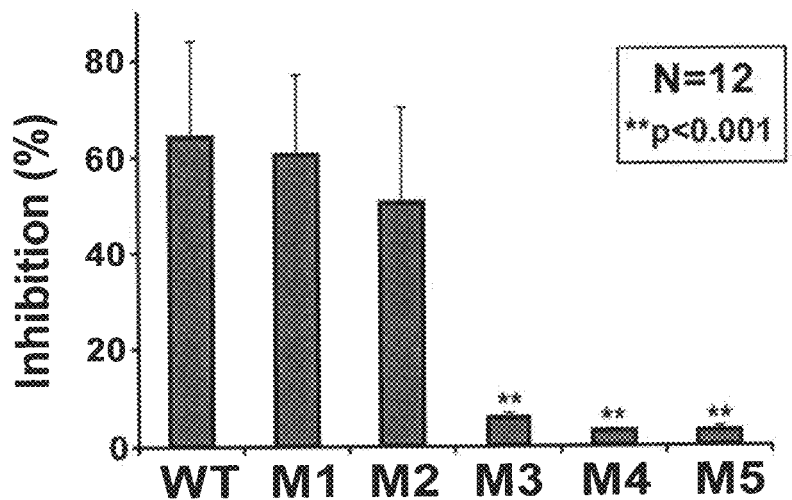
Figure 5:
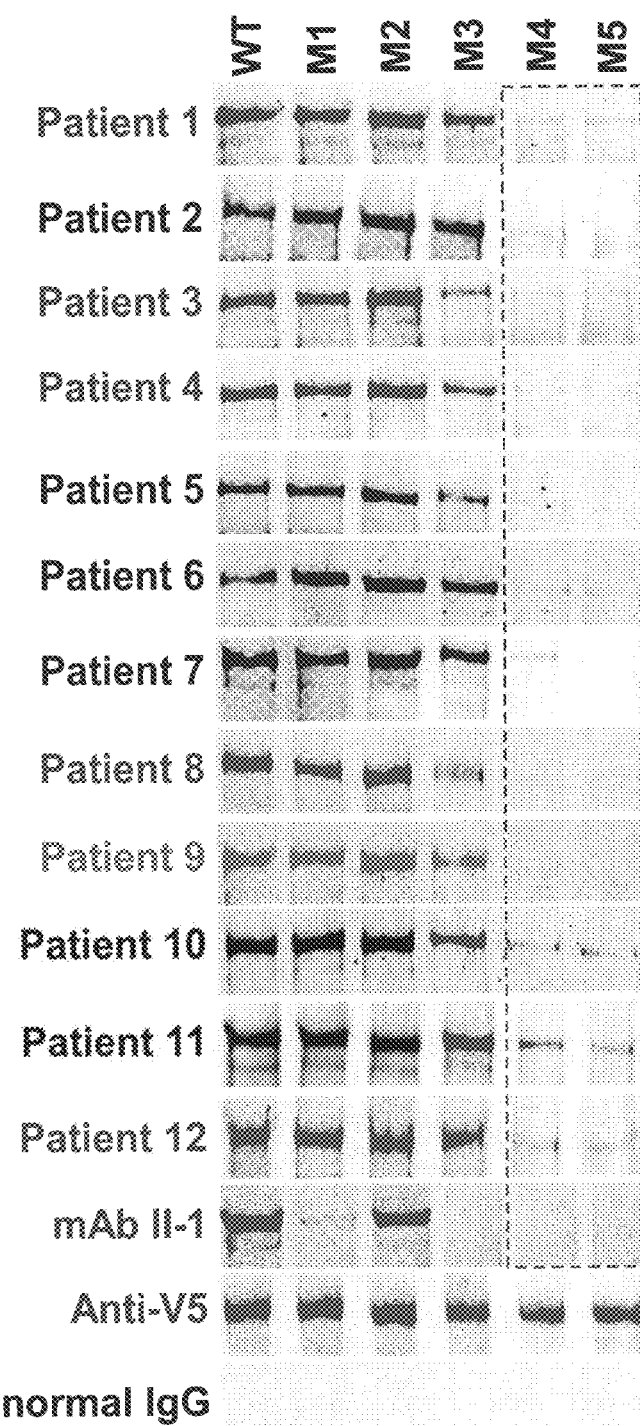
FIG. 5. Binding of anti-ADAMTS13 IgG autoantibodies from TTP patients ADAMTS13 and variants. Wild-type ADAMTS13 (WT) or ADAMTS13 variants (M1-M5) (50 ng) were incubated with a human monoclonal anti-spacer IgG (mAb II-1) (35 μM) or TTP patient plasmas (5-10 μl each, depending on plasma IgG concentrations). The immune complexes were pulled down with protein A-Sepharose 4B and detected by Western blotting with monoclonal anti-V5. The anti-V5 IgG-coupled Sepharose 4B beads were used for a positive control. Normal IgG was used for a negative control.

Binding of Patient Anti-ADAMTS13 IgG to Recombinant ADAMTS13 and Variants:

To determine whether the resistance of ADAMTS13 variants to autoantibodies was the result of impaired binding interactions between ADAMTS13 variants and autoantibodies, we performed immunoprecipitation followed by Western blotting assay as described previously[13;19]. As shown, mAb II-1 bound to WT and M2 consistently, but not to M1, M3, M4, and M5 (FIG. 5). This result was in a complete agreement with the antibody inhibitory activity (FIG. 4A).

Moreover, plasma polyclonal anti-ADAMTS13 IgGs from all 12 acquired idiopathic TTP patients also bound consistently to WT, M1, and M2, variably to M3, but rarely to M4 and M5 (FIG. 5). As controls, IgGs from healthy donors did not bind WT and variants detectably, while anti-V5 IgG bound to all constructs (FIG. 5). These results indicate that the inhibitory activity of either monoclonal or polyclonal anti-ADAMTS13 IgGs from TTP patients is mediated through their direct binding to exosite 3 in the spacer domain of ADAMTS13.

Model of Interactions Between ADAMTS13 and VWF:

To gain insight into the mechanisms underlying the enhanced activity of ADAMTS13 variants, we performed molecular modeling using the existing crystal structure of ADAMTS13-DTCS fragment (FIG. 6A)[29] and VWF-A2 domain[30]. As shown, the spacer domain comprises ten β-sheets (i.e. β1-10), a pocket formed by various β sheets containing a cluster of hydrophobic residues (L591, F592, L637, F638, L668, and T669), and a ring formed by Y661 and Y665 lined by basic residues R568, R589, R660, and R636 (FIG. 6B). This pocket appears to directly interact with the α6-helix (residues between D1653 and R1668) in the central A2 domain of VWF (FIG. 6D). The hydrophobic residues in the A2 domain presumably face exosite 3 to make strong hydrophobic contacts in conjunction with some hydrogen bonding outside of the pocket (data not shown). A substitution of R with K residue or Y with F residue or vice versa appears to alter the hydrophobicity of exosite 3 (FIG. 6C). The corresponding changes of the hydropathy index were noted as follows: R→K: −4.5→−3.9 and Y→F: −1.3→+2.8, thereby enhancing the interaction between VWF and ADAMTS13. Furthermore, a substitution of F592 with Y may open up the pocket even more, thereby better engaging substrate. There was also a corresponding backbone shift which appears to take place in the β2, β5, β6, and β9 sheets to compensate for the increased hydrophobicity (FIG. 6C). These changes allow greater engagement of exosite 3 with the A2 domain, particularly the amino acid residues between residues D1653 and R1668 (data not shown). Together, our findings suggest that the modification of an exosite in the spacer domain is a viable approach to improve ADAMTS13 function while reducing autoantibody binding and inhibition.

Discussion

In the present study, we have demonstrated that a positively charged residue i.e. arginine or lysine at the position 660 is critical for ADAMTS13 function (FIG. 1). This observation promotes us to test a hypothesis that replacement of the critical residues in the exosite in the spacer domain may generate ADAMTS13 variants that are resistant to binding and inhibition by autoantibodies from patients with acquired TTP, while preserving proteolytic activity. Of 24 ADAMTS13 variants prepared, two (i.e. M4 and M5) exhibited dramatically enhanced specific activity cleaving VWF73 peptide (FIG. 2) and multimeric VWF (FIG. 3). More interestingly, these two gain-of-function variants are more resistant than WT and several other variants to inhibition by monoclonal and polyclonal autoantibodies against ADAMTS13 in patients with acquired idiopathic TTP (FIG. 4 and Table 1). As shown, 10/12 TTP patient plasmas (83%) do not appear to inhibit proteolytic activity of M4 and M5, while the same amount of plasma completely inhibits proteolytic activity of WT, M1, and M2, but variably M3 under the same conditions. Plasmas from two patients weakly inhibit M4 and M5 activity (Table 1). These results further confirm using the gain-of-function rather than loss-of-function approaches described in the literature[18;28] the critical role of the exosite in the spacer domain in substrate recognition and proteolytic cleavage of VWF. Molecular modeling of interaction between VWF A2 and spacer domain shows that α5-helix of VWF A2 domain appears to directly interact with the residues in the exosite 3 (FIG. 6 and data not shown), primarily through hydrophobic interactions. A substitution of the residues R, F, R, Y, and Y with K, Y, K, F, and F at the positions of 568, 592, 660, 661, and 665, respectively, appears to increase hydropathy, thereby hydrophobic inter-

TABLE 1

Clinical characteristics, plasma ADAMTS13 activity, inhibitors of TIP patients, and sensitivity of WT ADAMTS13 and novel variants to the inhibition by patient plasma

| Patient no. | Age, y | Sex | Platelet count, $\times 10^{9/L}$ | Hematocrit, % | LDH, U/L | Creatinine, mg/dL | CNS, signs and symptoms | ADAMTS13 activity by rF-vWF73, % | Plasma anti-ADAMTS13 Inhibitors | Plasma anti-ADAMTS13 IgG, U/mL | Sensitivity to patient plasma inhibition | | | | | |
|---|---|---|---|---|---|---|---|---|---|---|---|---|---|---|---|---|
| | | | | | | | | | | | WT | M1 | M2 | M3 | M4 | M5 |
| 1 | 44 | Female | 15 | 23 | 695 | 1.1 | Yes | <5 | + | 84.2 | + + | + + | + + | + | − | − |
| 2 | 56 | Female | 19 | 29 | 854 | 1.1 | Yes | <5 | + | 35.4 | + + | + + | + + | + | + | + |
| 3 | 45 | Female | 88 | 28 | 995 | 0.7 | Yes | <5 | + | 81.9 | + + | + + | + + | − | − | − |
| 4 | 52 | Female | 52 | 20 | 866 | 1.1 | Yes | <5 | + | 132.0 | + + | + + | + + | − | − | − |
| 5 | 79 | Female | 7 | 27 | 1660 | 1.4 | Yes | <5 | + | 118.0 | + + | + + | + + | + | − | − |
| 6 | 34 | Male | 15 | 23 | 2703 | 0.9 | Yes | <5 | + | 127.5 | + + | + + | + + | + | − | − |
| 7 | 34 | Male | 0 | 33 | 859 | 1.9 | No | <5 | + | 162.0 | + + | + + | + + | − | − | − |
| 8 | 23 | Female | 11 | 18 | 3412 | 0.8 | Yes | <5 | + | 132.0 | + + | + + | + + | − | − | − |
| 9 | 42 | Female | 23 | 17 | 3259 | 0.8 | Yes | <5 | + | 168.0 | + + | + + | + + | − | − | − |
| 10 | 21 | Female | 9 | 13 | 1489 | 1.5 | Yes | <5 | + | 72.0 | + + | + + | + + | + | + | + |
| 11 | 61 | Female | 33 | 28 | 511 | 0.8 | Yes | <5 | + | 221.0 | + + | + + | + + | − | − | − |
| 12 | 42 | Male | 16 | 24 | 6517 | 1.2 | No | <5 | + | 147.2 | + + | + + | + + | + | − | − |
| N = 12 | 43* | | 15.5* | 23.5* | 1242* | 1.1* | (83.3) | (100) | (100) | (100) | (100) | (100) | (100) | (50) | (17) | (17) |

Figure 6:
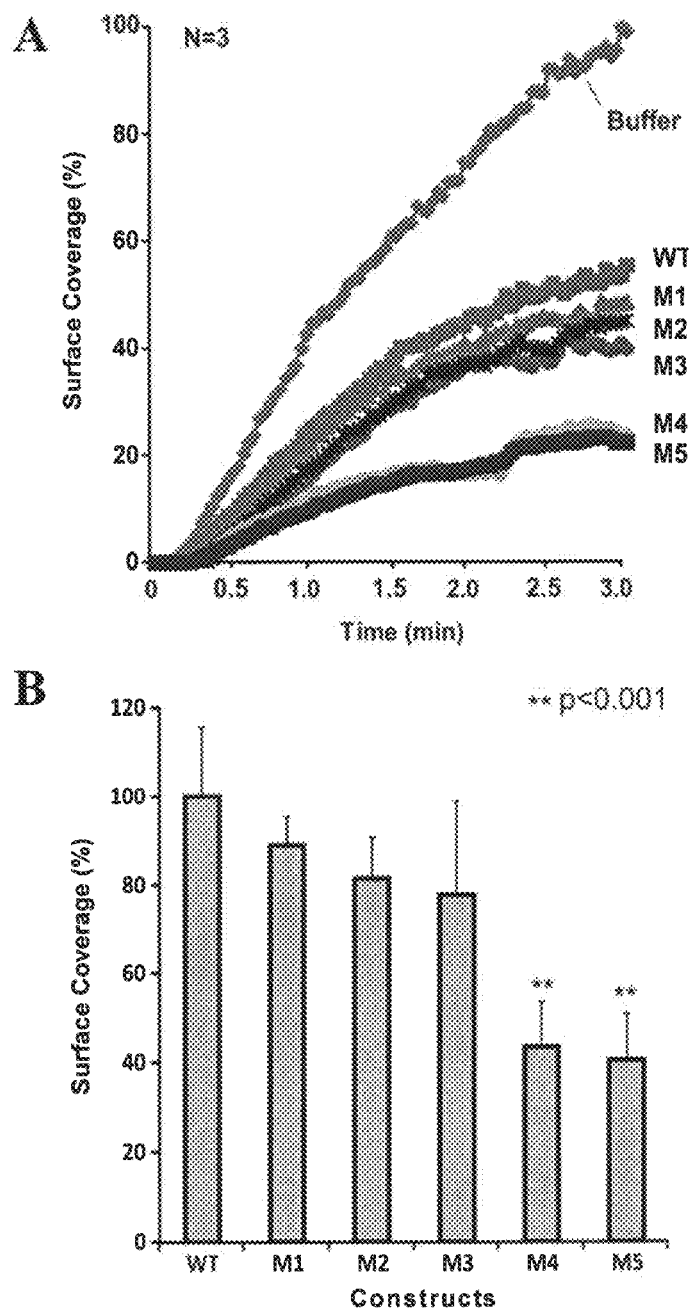
FIG. 6. WT and variants of ADAMTS13 inhibited platelet aggregation on collagen-coated surface under flow. Whole blood (anti-coagulated with PPACK) was incubated with AlexaFlur488 conjugated anti-CD41 IgG (1 μg/ml) and WT-ADAMTS13 or variants (10 nM) for 15 min. The blood was then flown through collagen-coated surface in a microfluidic device at 10 dyne/cm$^2$ for 3 min. The rate and amount of platelets accumulated on the surface were determined under an inverse fluorescent microscope with a high speed CCD camera (FIG. 6A). Data were analyzed by the BioFlux Mortage software. The mean percentages of the platelet coverage from three independent experiments (n=3) at 1.5 minutes were plotted against the various ADAMTS13 variants added (FIG. 6B).
Figure 7:
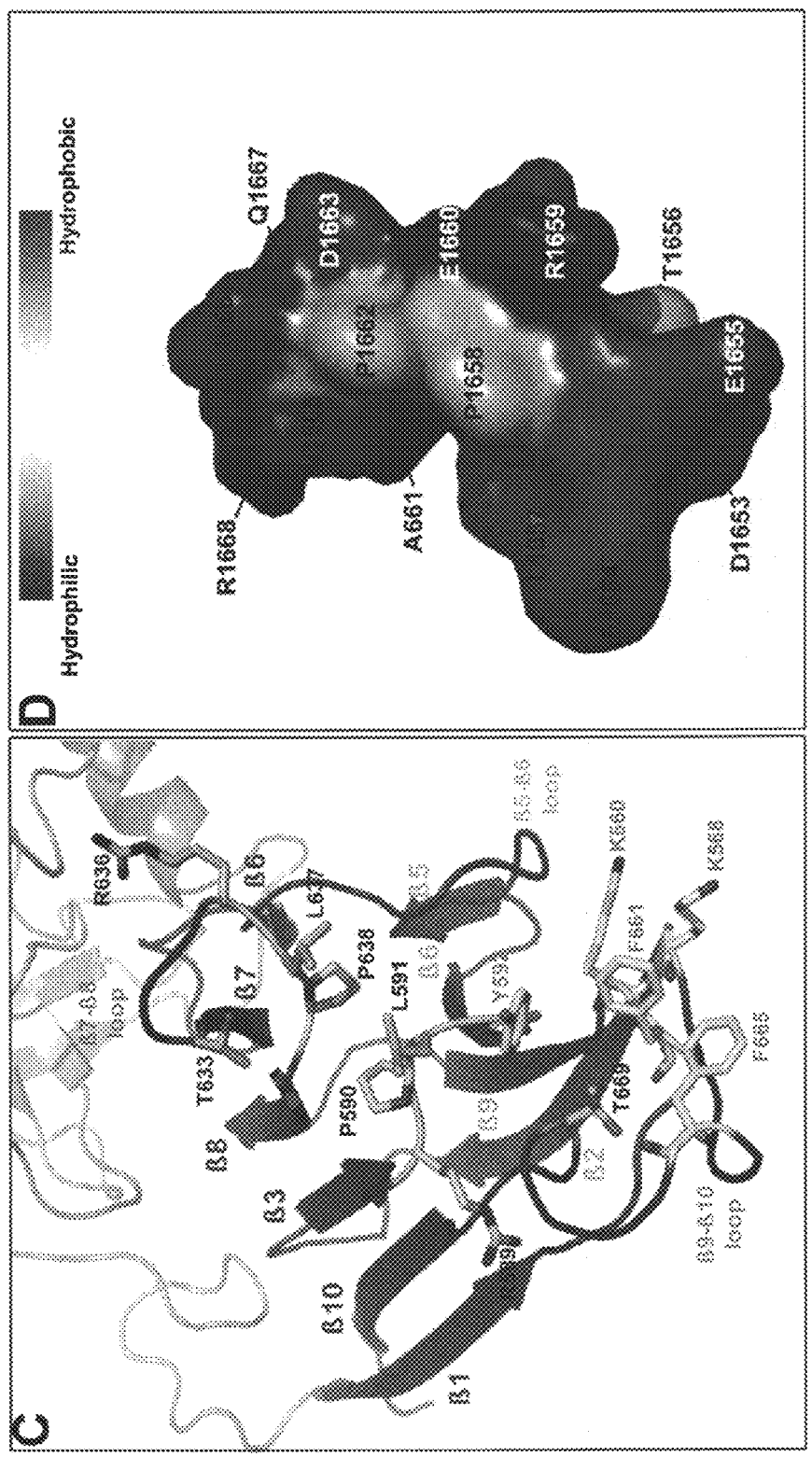
FIG. 7. Modeling of ADAMTS13-spacer and VWF-A2 interaction.
Figure 7:
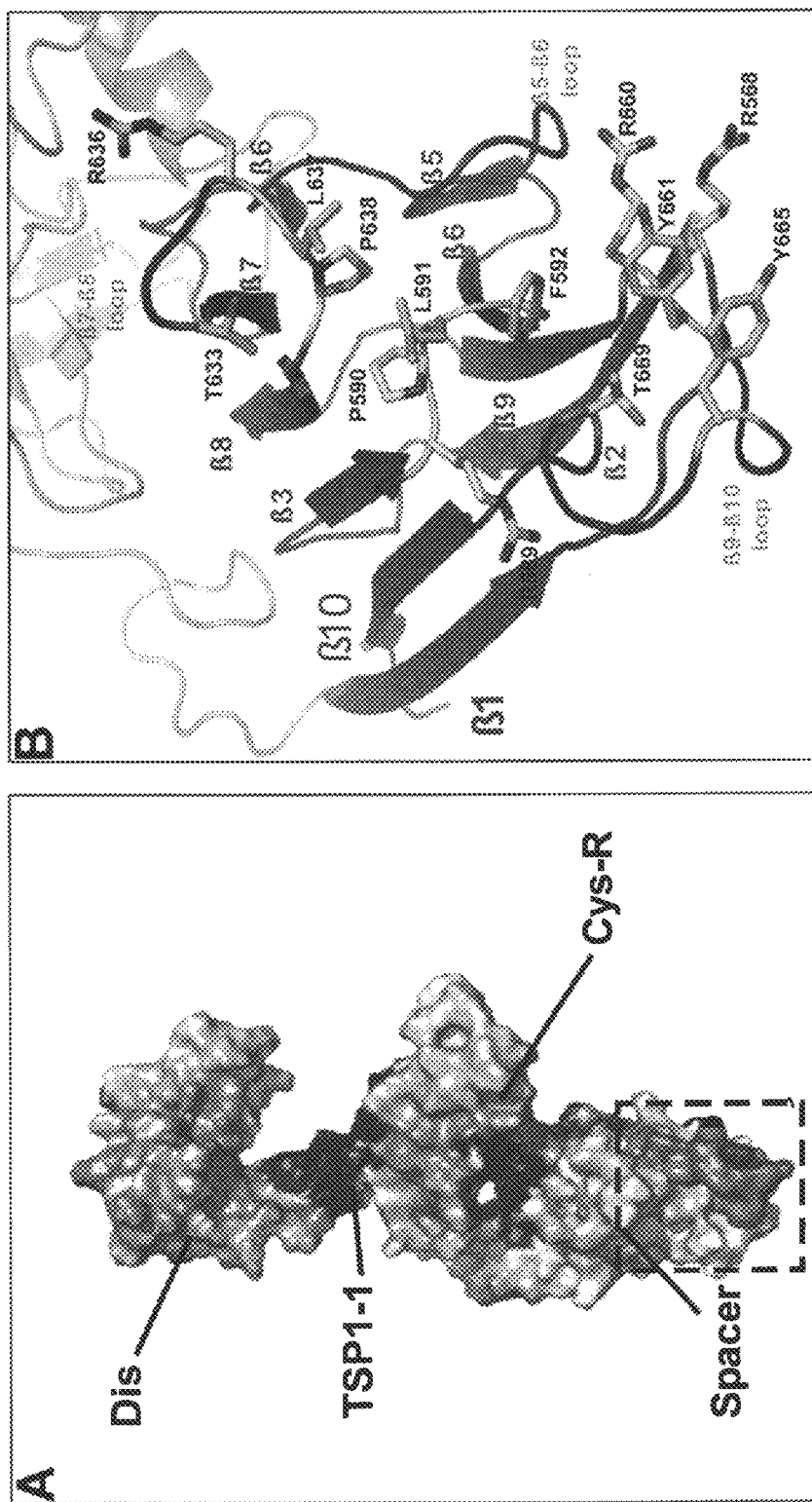

Values In parentheses indicate positive rates in percentages.
LDH indicates lactate dehydrogenase: −, negative inhibition (<10% reduction in activity);
+, mild inhibition (10%-30% reduction in activity);
+ +, moderate inhibition (30%-50% reduction in activity);
and + + +, strong inhibition (>50% reduction in activity) after 50:50 mixing with patient plasma.
*Median values.

actions between the exosite 3 and α5-helix of the central A2 domain (FIG. 6 and data not shown).

Our findings also provide novel insight into the mechanism underlying pathogenesis of acquired idiopathic TTP caused by anti-ADAMTS13 autoantibodies. Despite polyclonal nature of autoantibodies against ADAMTS13 in patients with TTP[13;31], the inhibitory activity of anti-ADMTS13 autoantibodies appears to be largely mediated through their binding to the exosite 3 in the spacer domain, as an alteration in this region dramatically reduced binding of anti-ADAMTS13 IgGs (FIG. 5) and inhibition by patient plasma autoantibodies (FIG. 4). Our results are consistent with those reported by Pos et al[19], in which a replacement of R568, F592, R660, Y661, and Y665 with A abolishes the binding of anti-ADAMTS13 IgGs from most TTP patients[19]. However, alanine substitution results in loss-of-function of ADAMTS13 variants, which have no values therapeutically.

Our findings could change the way we treat acquired TTP with inhibitors. To date, plasma exchange remains the main treatment for acquired TTP patients[32;33]. Plasma exchange alone is found to be inadequate to restore deficiency of plasma ADAMTS13 activity and remove autoantibodies against ADAMTS13[33]. Infused wild type ADAMTS13 may be rapidly neutralized by IgG autoantibodies, rendering patients persistent deficiency of plasma ADAMTS13 activity. Low plasma ADAMT13 activity and persistence of anti-ADAMTS13 IgGs correlate with an increased rate of relapse[11;33;34]. Other immunosuppressive therapies such as cyclosporine[35;36], cyclophosphamide[37;38], rituximab (anti-CD20 antibody)[37;38] may reduce the antibody formation, but take weeks to months to have an effect. Therefore, autoantibody-resistant ADAMTS13 variants may have a value to instantaneously restore plasma ADAMTS13 activity when plasma exchange is not readily available or delayed. The infused ADAMTS13 variants are likely to work despite polyclonal nature of anti-ADAMTS13 IgGs. The affinity of anti-ADAMTS113 IgGs in patients with TTP toward various other domains besides spacer domain is relatively weak[13-15;31] the clearance of plasma ADAMTS13 as a result of binding by non-inhibitory IgGs does not appear to be the primary mechanism underlying severe deficiency of plasma ADAMTS13 activity in patients with acquired TTP[39].

We conclude that subtle alterations of the exosite binding site in the spacer domain represent a viable strategy for engineering of ADAMTS13 variants with preserved or enhanced proteolytic activity but resistant to inhibition by anti-ADAMTS13 autoantibodies in patients with acquired idiopathic TTP. The gain-of-function variants provide a novel tool for understanding of the critical role of exosite interaction for proteolysis of VWF by ADAMTS13. Furthermore, the antibody-resistant variants underscore the importance of exosite 3 and adjacent residues in the spacer domain in pathogenesis of acquired TTP caused by autoantibodies against ADAMTS13. Finally, we hope that these variants with desired properties to be further developed for therapy of acquired TTP with inhibitors.

Example II

Identification of a Novel Exosite ($Glu^{634}$-$Arg^{639}$) in the Spacer Domain of ADAMTS13 Required for Recognition of Von Willebrand Factor As mentioned above, exosite binding plays a key role in cleavage of VWF by ADAMTS13 (A Disintegrin And Metalloprotease with ThromboSpondin type 1 repeats, 13). Two exosites that are evolutionarily conserved from zebra fish to mammals have been identified in the spacer domain by sequence alignment. Example I provides data showing that exosite 3 in the spacer domain plays a critical role for substrate recognition (*Blood* 115: 2300-10, 2010), and modification of this exosite generates ADAMTS13 variants with improved specific activity but reduced autoantibody binding (*Blood* 119:3836-43, 2012).

Figure 8:
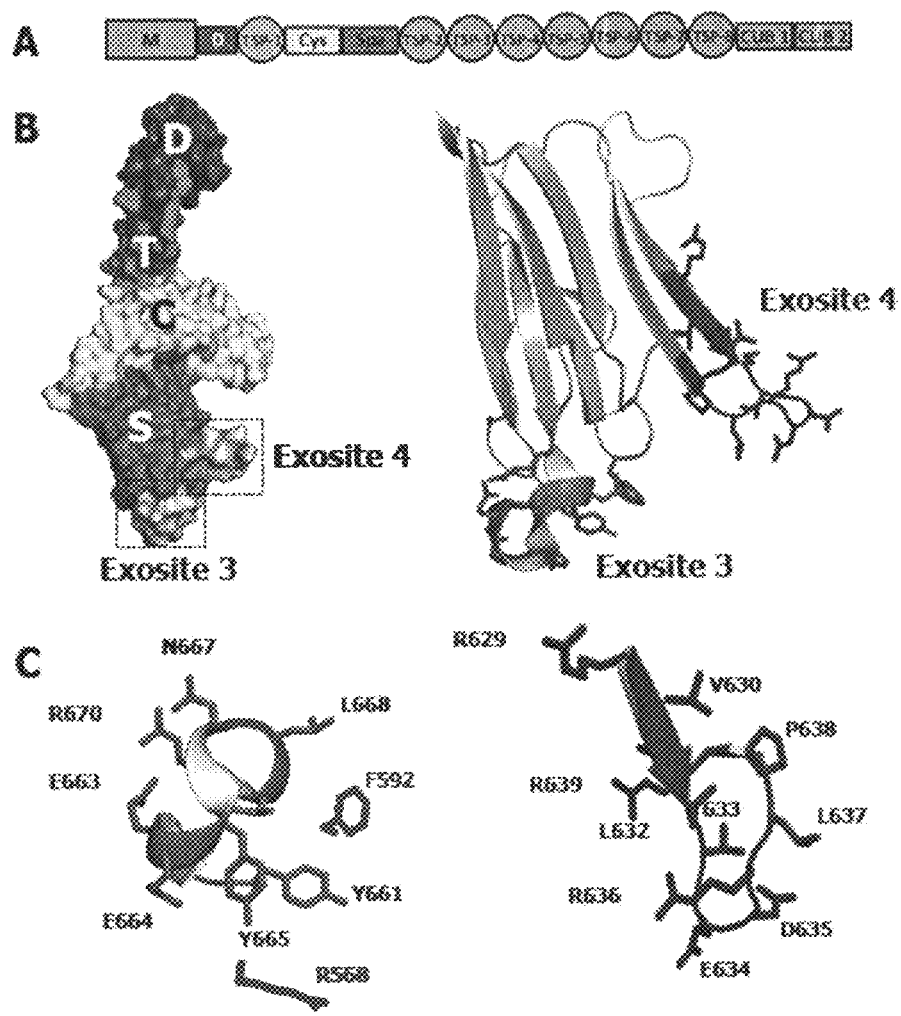
FIG. 8.
Figure 9A:
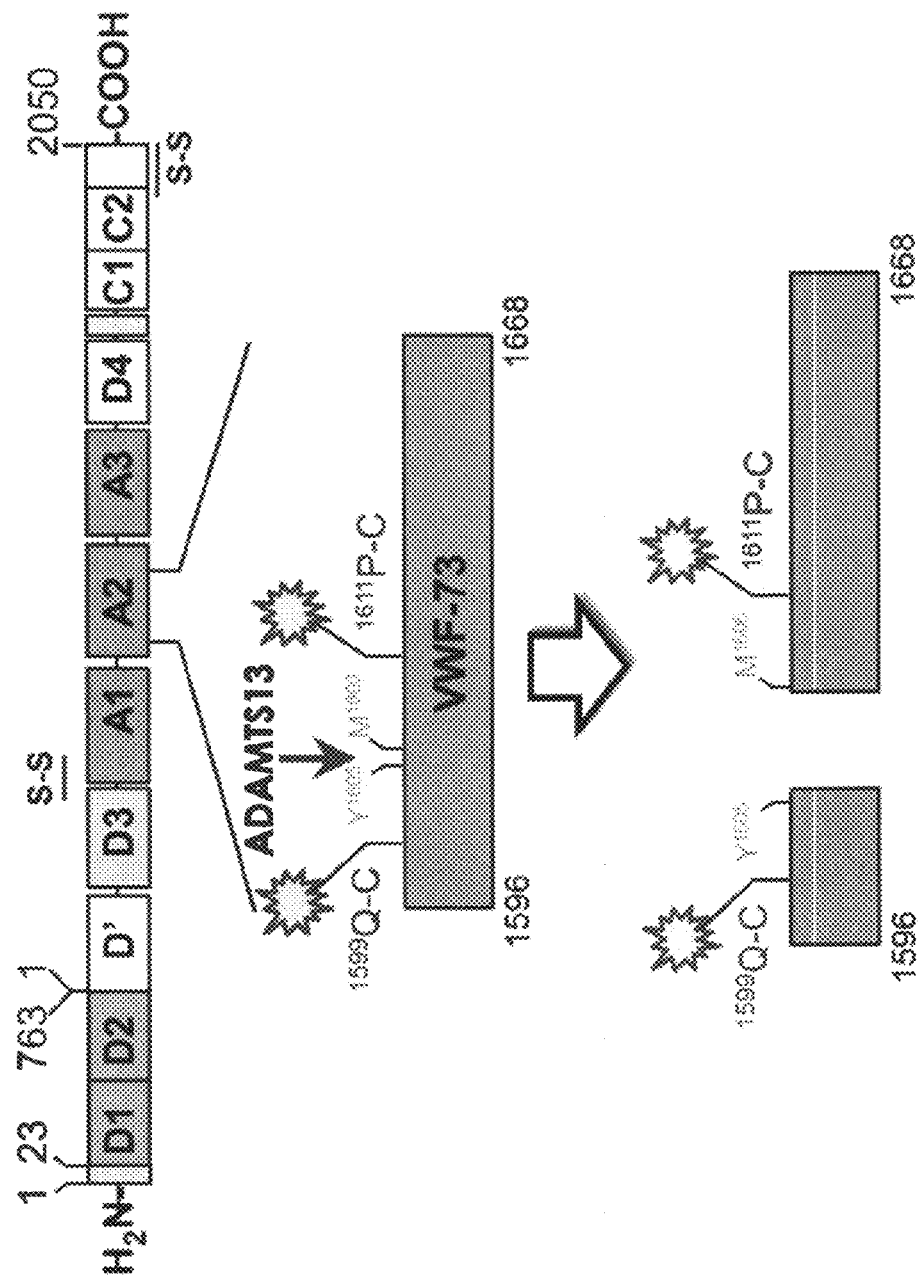
FIG. 9A) Schematic of VWF-73 FRETS assay. Residues corresponding to Q1599 and P1611 in the A2 domain of VWF are mutated to cysteines and labeled by fluorescein-5-maleimide. These residues are homoquenchers that fluoresce upon cleavage by ADAMTS13.
Figure 9B:
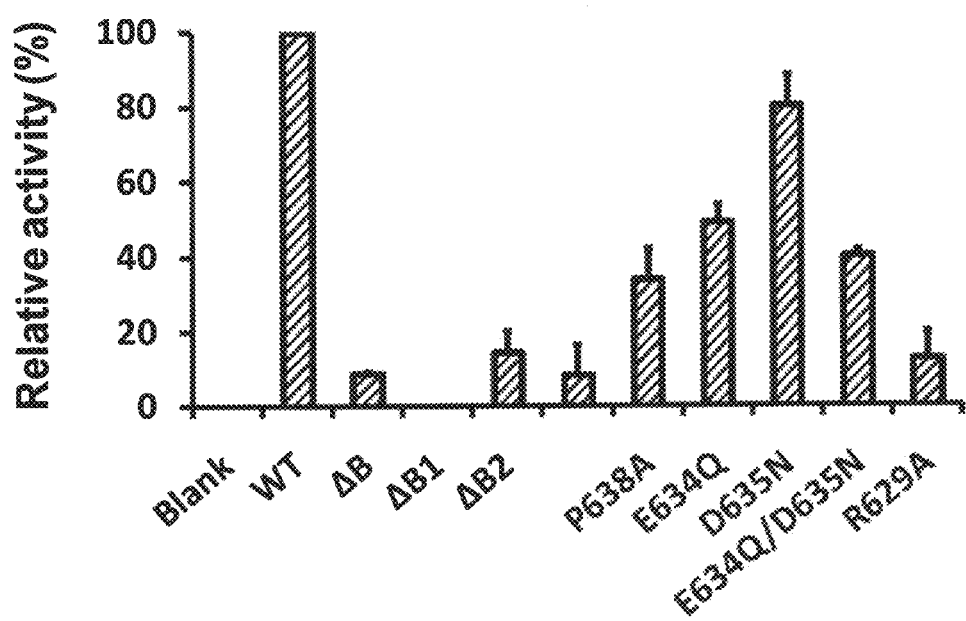
FIG. 9B) VWF-73 FRETS assay of motif B variants. Concentration of VWF-73 peptide=2 μM; various concentrations of variants are assayed and quantified relative to the wild type activity. ΔB=$^{632}$LTEDRLPR$^{639}$→Deleted, ΔB1=$^{632}$LTED$^{635}$→Deleted, and ΔB2=$^{636}$RLPR$^{639}$→Deleted. ΔB1 is not secreted, so data could not be obtained for this variant.
Figure 10:
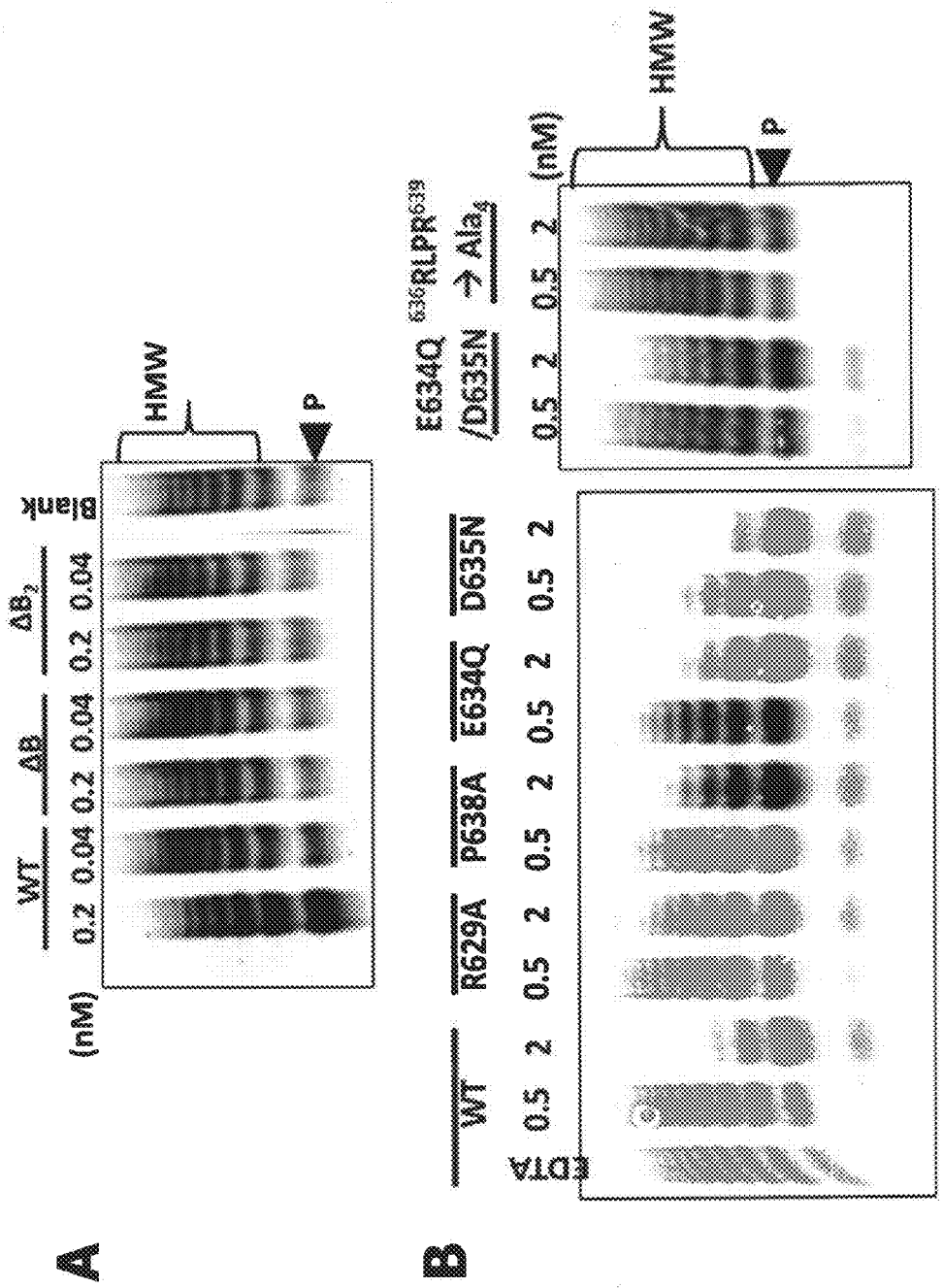
FIG. 10.
Figure 11C:
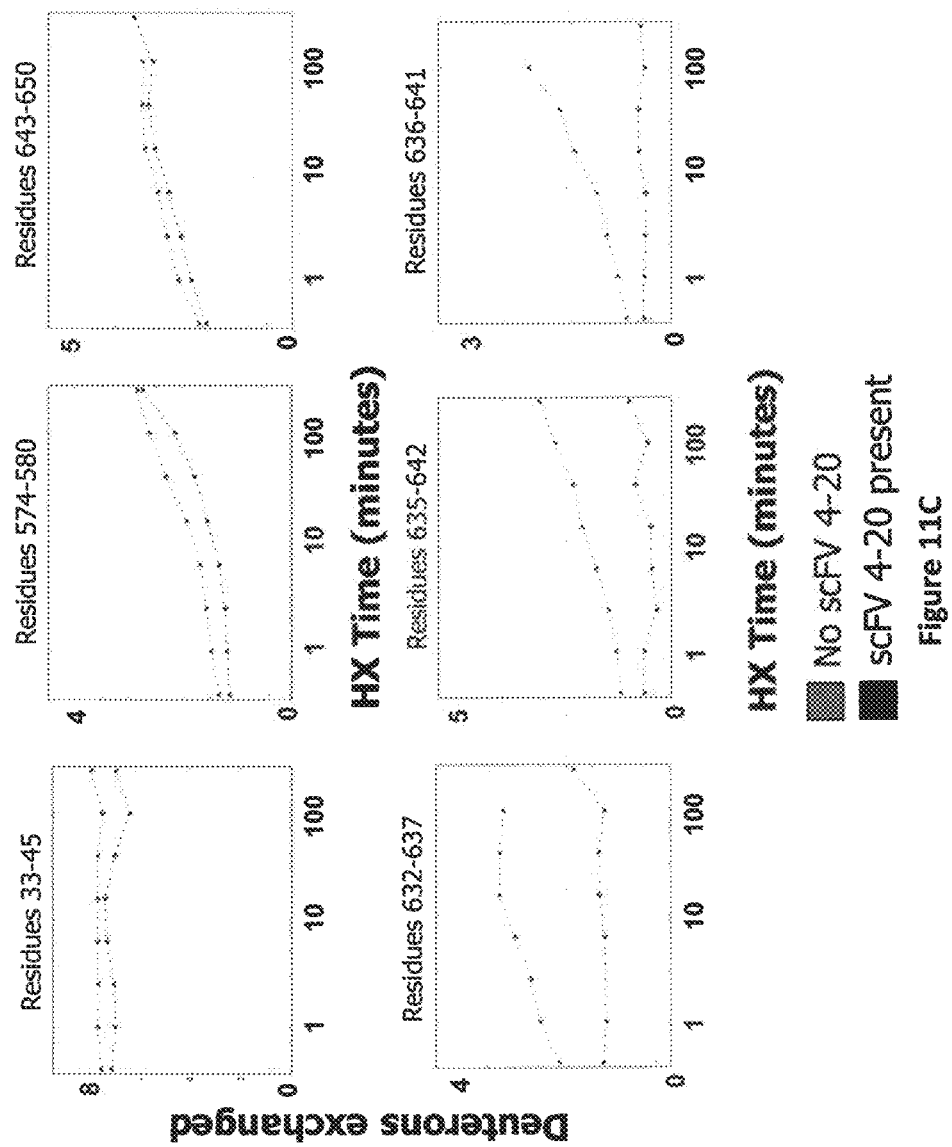
FIG. 11C) Results of hydrogen exchange from a few representative peptides. Residues 33-45 are in the metalloprotease domain and exchange readily with or without scFV 4-20 present. Residues 574-580 and 643-650 are in the spacer domain but show no interaction with scFV 4-20. Residues 632-637, 635-642, and 636-641 have decreased exchange with scFV 4-20, indicating an interaction.
Figure 12:
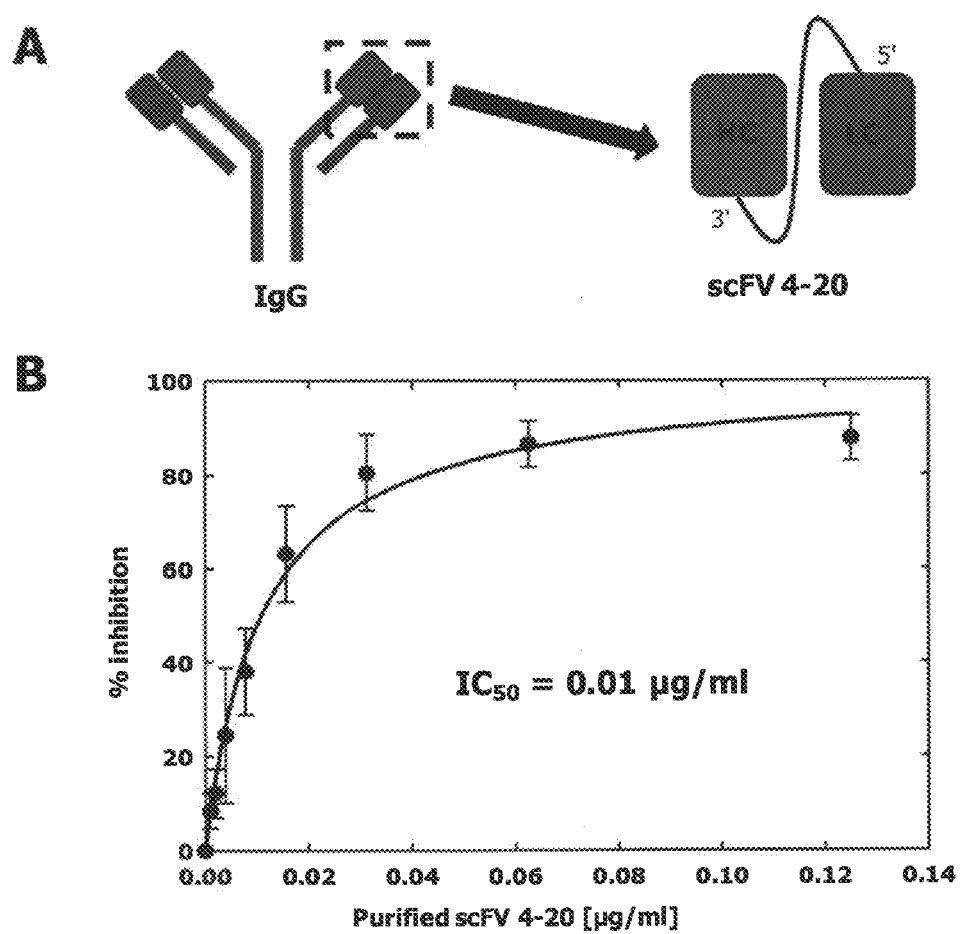
FIG. 12.

In the present study, using a site-directed mutagenesis approach, we identified a novel exosite near exosite 3 in the spacer domain, termed exosite 4, a region between residues $Glu^{634}$ and $Arg^{639}$. See FIG. 8. A partial (DEx4a:deletion of Leu632-Asp635 or DEx4b:deletion of Arg636-Arg639) or complete deletion of the exosite (DEx4) significantly impaired proteolytic activity towards peptidyl VWF73 and multimeric VWF. See FIGS. 9, and 10. Moreover, substitution of all surface exposed residues in Ex4A (LTED/AAAA) or Ex4b (RLPR/AAAA) with alanine had a similarly detrimental effect on proteolytic activity. However, a deletion or mutation of $^{632}LTED^{635}$ to alanines caused intracellular retention of the enzyme. Further studies using deuterium-hydrogen exchange and mass spectrometry demonstrated that the residues (D632-E642) were targeted by a human monoclonal antibody (scFV4-20) isolated by phage display from an acquired TTP patient. See FIGS. 11 and 12.

Figure 13:
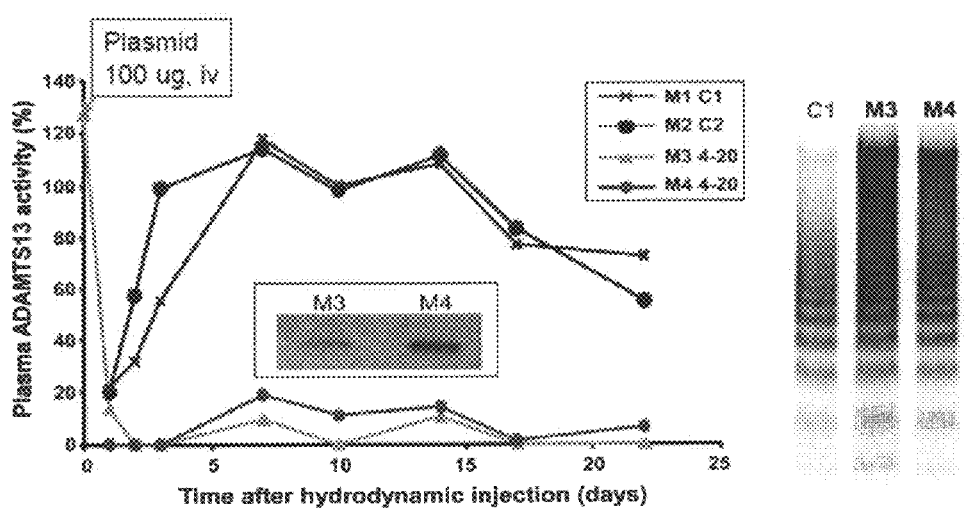
FIG. 13. Inhibition of murine ADAMTS13 activity and alteration of VWF multimers by scFv 4-20.
Figure 14:
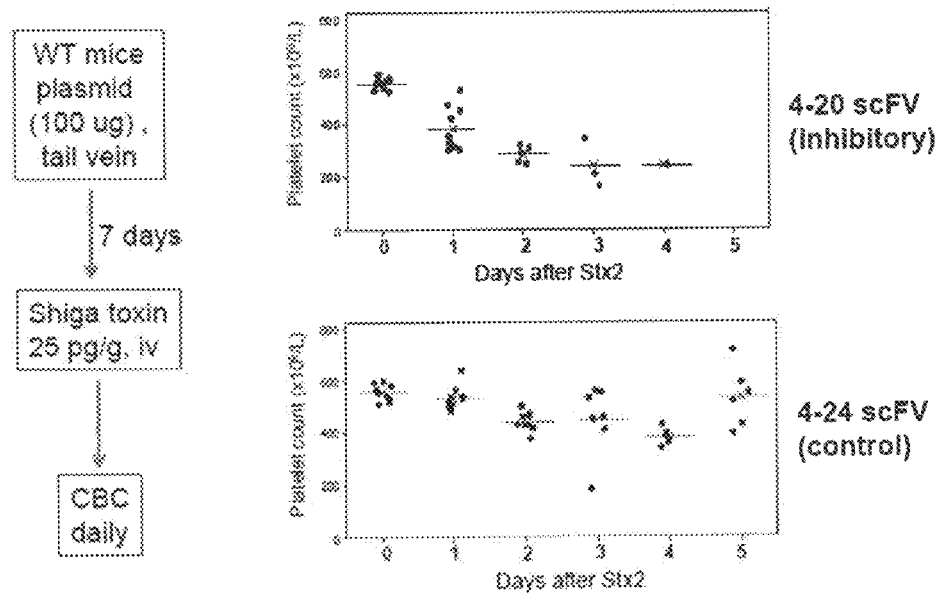
FIG. 14. 4-20 mAb causes acquired TTP triggered by bacterial shigatoxin. Plasmid pLIVE containing cDNA sequence of 4-20 mAb against ADAMTS13 was introduced into wild-type mice (CAST/Ei strain) via a hydrodynamic injection. 4-20 mAb was expressed in liver and secreted into blood stream. 10 days after injection, mice were challenged with Shigatoxin-2 and complete blood counts were determined daily for 7 days. Mice with 4-20 mAb expression developed thrombocytopenia, while control mice did not.

FIG. 13 shows inhibition of murine ADAMTS13 activity and alteration of VWF multimers by scFv 4-20. FIG. 14 shows that 4-20 mAb causes acquired TTP triggered by bacterial shigatoxin. FIG. 15 is a graph showing survival rates in mice expressing control and inhibitory scFV after being challenged with shiga toxin.

We conclude that the region between residues Leu632 and Glu642 is a novel exosite necessary for recognition and cleavage of VWF and appears to be important for autoantibody binding in the case of TTP. Further studies demonstrated that the residues Asp635 and Arg636 in exosite 4 play a critical role for substrate recognition. We conclude that the region between residues Glu634 and Arg639 is a novel exosite necessary for recognition and cleavage of VWF.

Example III

Figure 16:
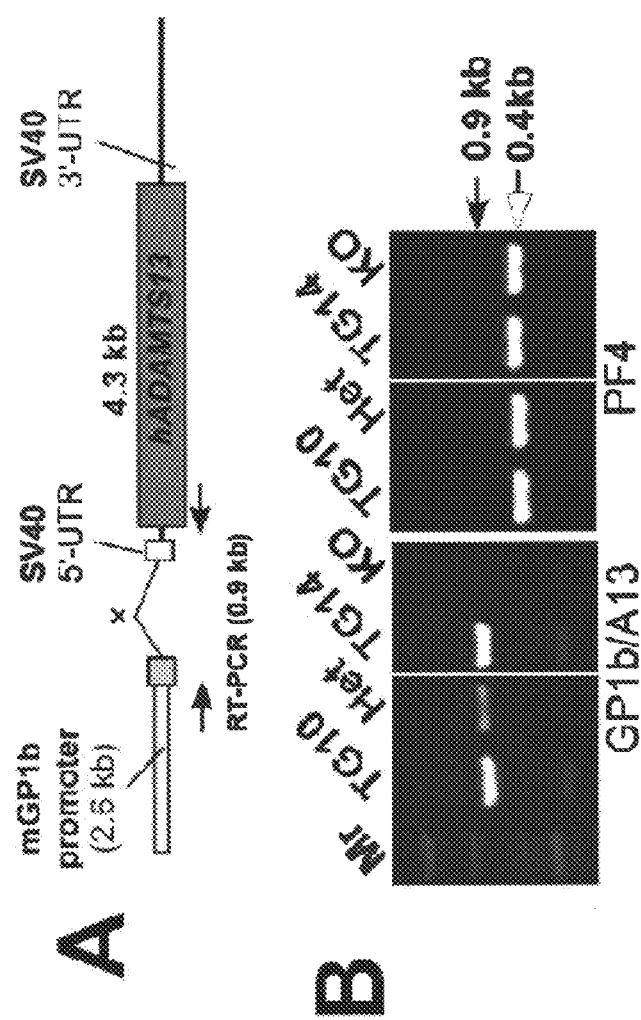
FIG. 16. ADAMTS13 construction and expression in platelets. Construct used in the transgenic mice (FIG. 16A); expression of GP1b/ADAMTS13 transgene or platelet factor 4 (PF4) mRNA (FIG. 16B); expression of ADAMTS13 and GP1b in platelets of WT, KO and transgenic mice (TG) (FIG. 16C); expression of ADAMTS13 (arrowhead) in transgenic mice by Western blotting (FIG. 16D); co-localization of human rA13 and endogenous VWF in platelets and megakaryocytes (E).
Figure 16:
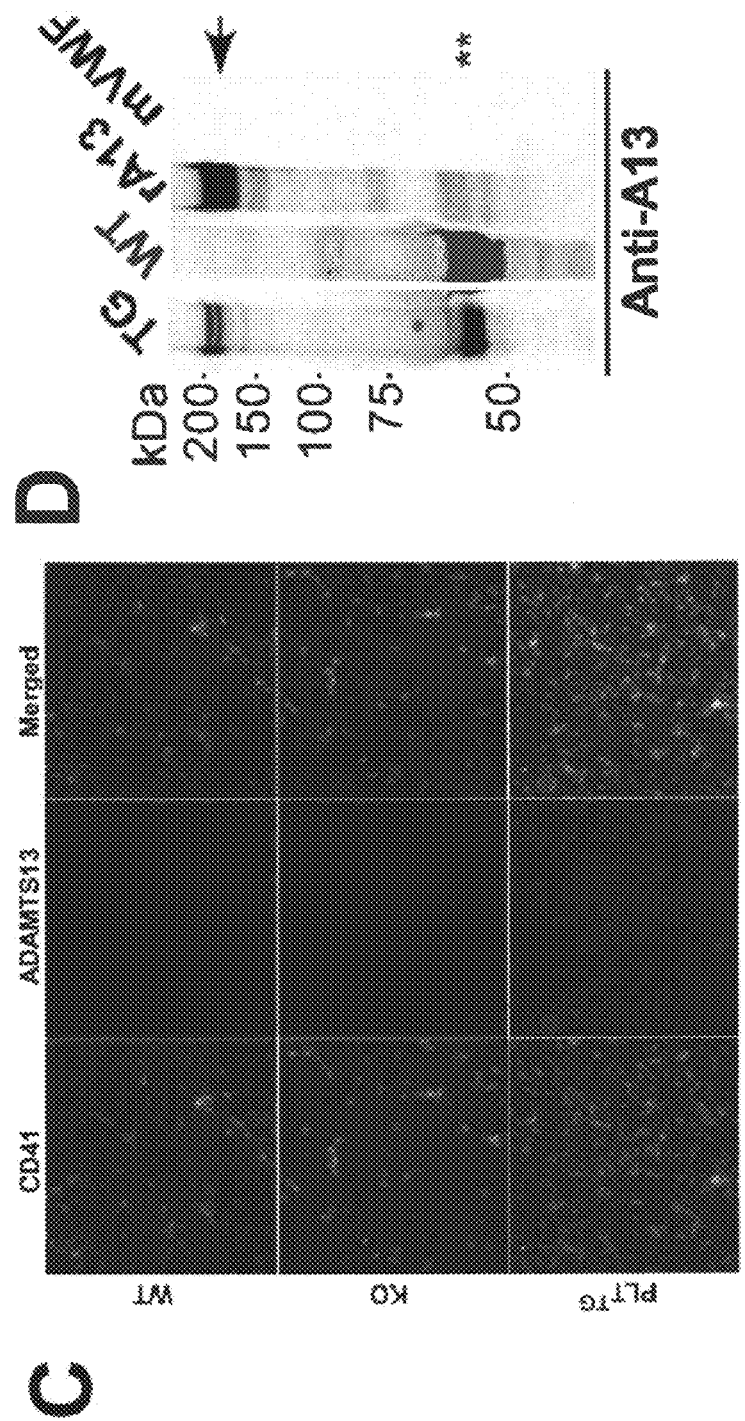
Figure 16:
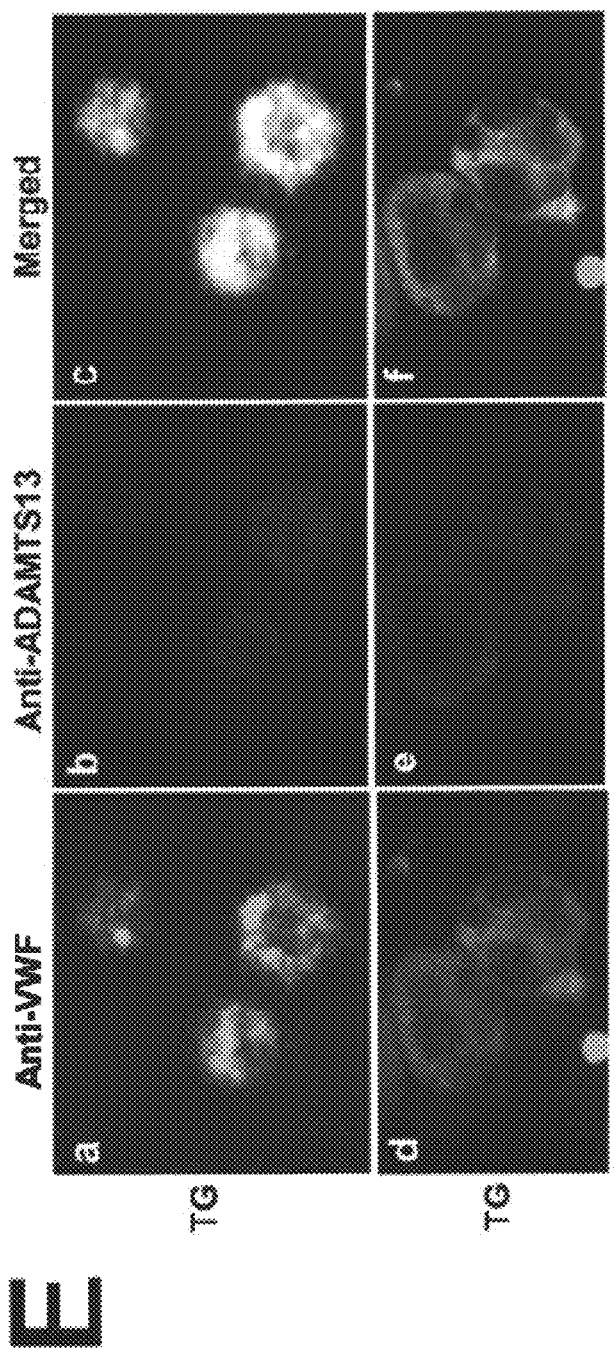

ADAMTS13 Expressed in Platelets Offer Systemic Protection Against Arterial Thrombosis and Murine Models of Thrombotic Thrombocytopenia Purpura To develop novel therapeutics against TTP, we tested a hypothesis that recombinant ADAMTS13 expressed specifically in platelets may offer protection against arterial thrombosis and, therefore, provide therapeutic benefits for TTP in the presence of inhibitors. We generated transgenic mice carrying a human full-length ADAMTS13 gene under a murine platelet glycoprotein 1b promoter (FIG. 16A). The transgenic mice were bred with Adamts13$^{-/-}$ (CAST/Ei) mice for greater than 4 generations. Reverse transcriptase-polymerase chain reaction revealed the expected band for GP1b/ADAMTS13 transgene in the transgenic mice but not the Adamts13$^{-/}$ mice (FIG. 163). Through immunohistochemical expression analysis, human ADAMTS13 was detected only in the transgenic mice (FIG. 16C). By Western blotting, a full-length human ADAMTS13 protein (approximately 195 kDa) was detected in platelet lysate from transgenic (rA13-Plt$^{TG}$) mice but not from WT mice (FIG. 16 D). And through immunohistochemistry, co-localization of human ADAMTS13 and endogenous VWF in platelets was strongly detected in the transgenic mice (FIG. 16E).

Figure 17:
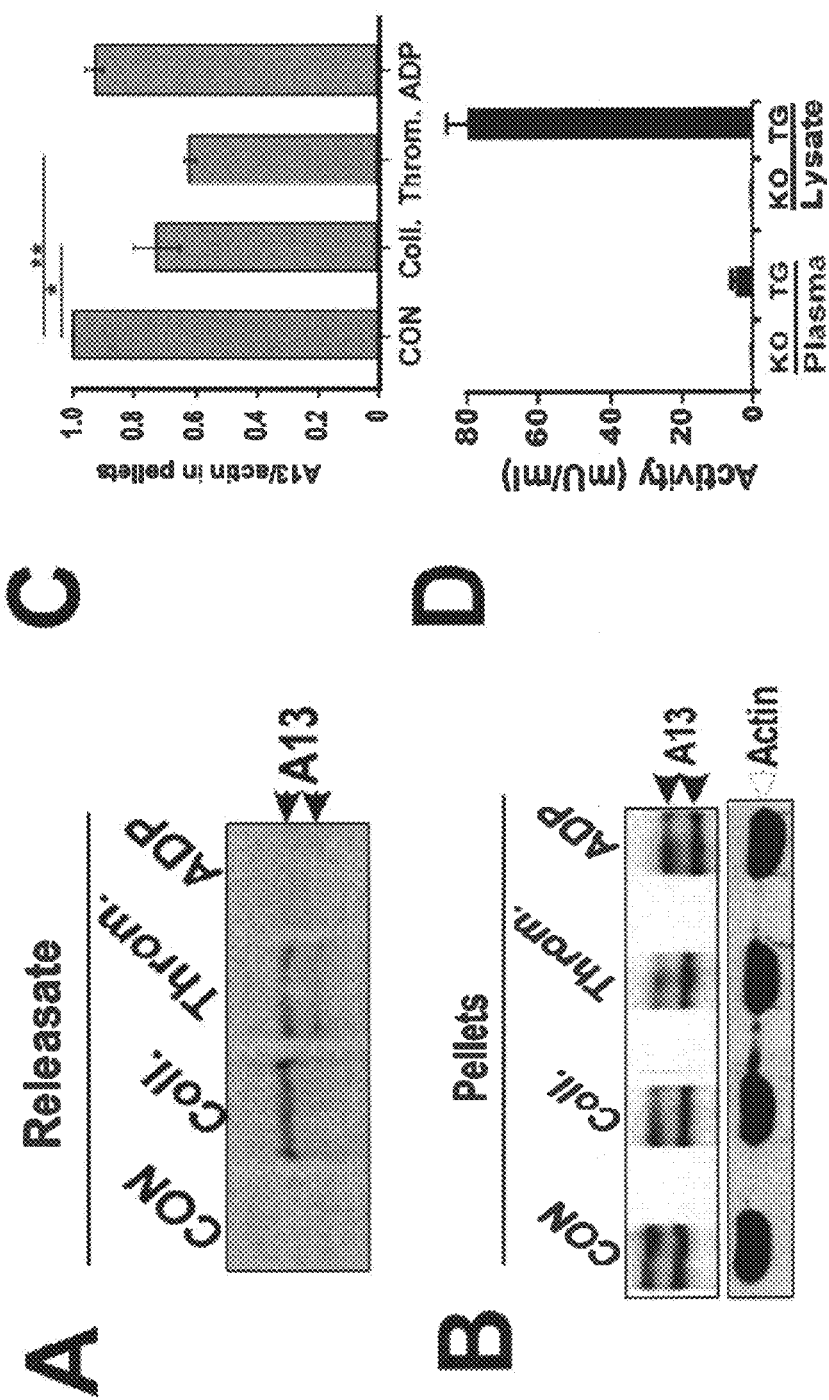
FIG. 17. ADAMTS13 secretion and activity in platelets and plasma of transgenic mice. Washed platelets from ADAMTS13−/− mice with or without platelet-expression of human recombinant ADAMTS13 were stimulated with collagen, thrombin, and 2 MeSADP for 5 min. The releasate (FIG. 17A) and platelets (FIG. 17B) were separated by centrifugation at 500×g for 10 min. Proteins were concentrated and detected by Western blotting; Quantification of relative amount of ADAMTS13/actin in platelets is shown (FIG. 17C); proteolytic activity in plasma and platelet lysate is detected by FRETS-VWF73 (D). Transgenic platelets expressing ADAMTS13 aggregate normally and secrete ADAMTS13 upon stimulation and aggregation. No ADAMTS13 was detected in Adamts13−/− platelets.

To assess ADAMTS13 secretion, platelets isolated from transgenic mice were stimulated with collagen, alpha-thrombin or 2MeSADP (FIG. 17). Releasate and platelets were separated and relative amounts of ADAMTS13/actin in platelets were detected by Western blot and densitometry analysis (FIG. 17 A-C). Little to no ADAMTS13 was detected in plasma of transgenic mice suggesting the expressed human ADAMTS13 is stored inside the platelets and only upon stimulation is the metalloproteinase released.

To determine the capacity for ADAMTS13 mediated proteolysis, activity assays were performed utilizing FRETS-VWF73 (FIG. 17D). Both plasma and lysate were examined from the Adamts13$^{-/-}$ and rA13-Plt$^{TG}$ mice. In the absence of stimulation, proteolytic activity was observed in the lysate of transgenic mice. No evidence of proteolysis was detected in the plasma of transgenic mice or in the plasma or lysate of the Adamts13$^{-/-}$ mice. These findings provide further support of the sequestration of ADAMTS13 inside platelets.

Figure 18:
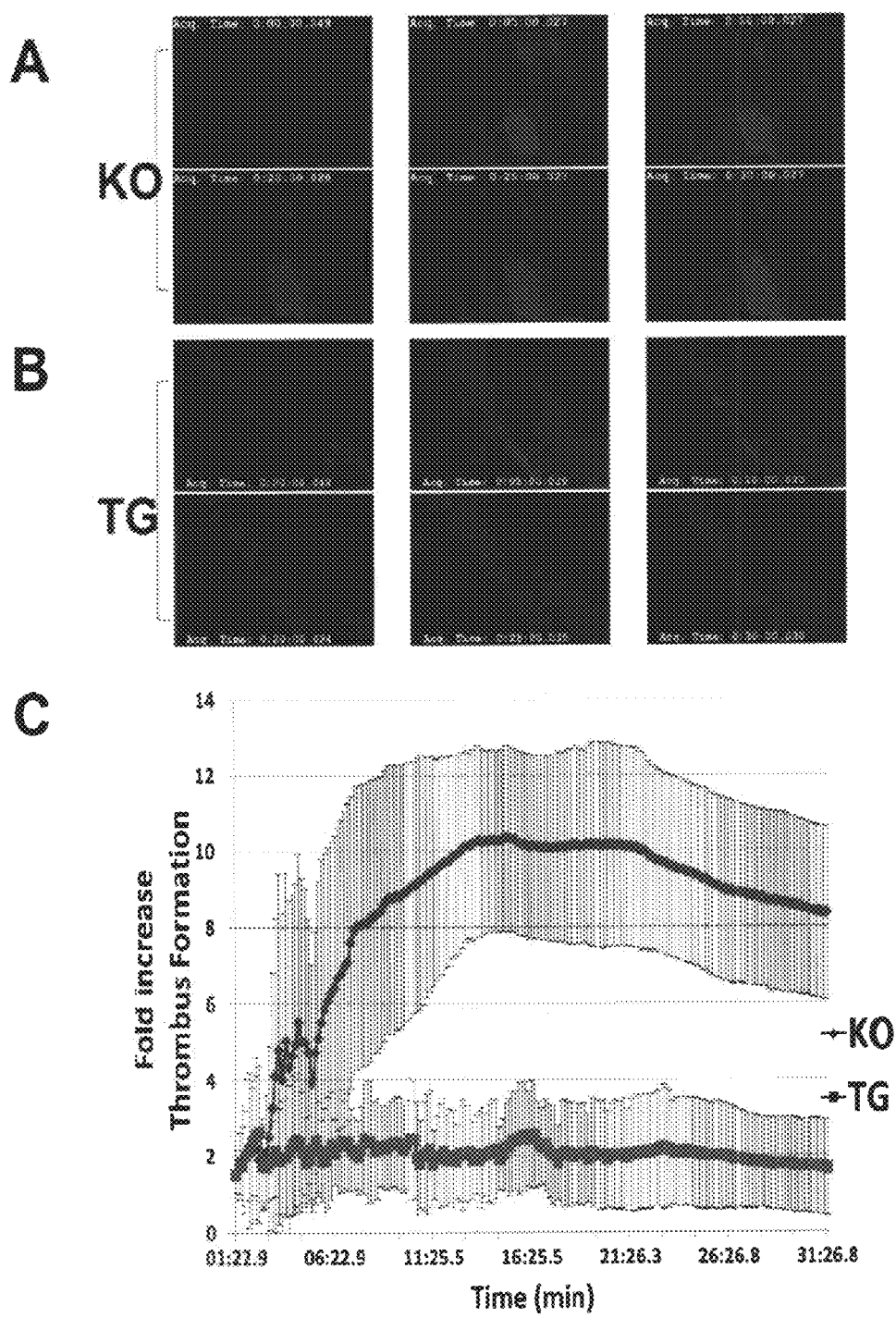
FIG. 18. Efficacy of platelet expression of ADAMTS13 on arteriole thrombosis. Intravital microscopic analysis for the rate of thrombus formation in murine mesenteric arterioles in mice after oxidative injury.

To examine the rate of thrombus formation in murine mesenteric arterioles of mice after oxidative injury, intravital microscopic analysis was performed (FIGS. 18A, B, and C). The mesenteric arterioles of knockout and transgenic mice were injured with 10% FeCL$_3$. Time-lapse images of thrombus formation were recorded and quantification of fluorescence intensity over time in the mesenteric arterioles was examined for knockout and transgenic mice. rA13-Plt$^{TG}$ mice exhibited a dramatically reduced rate of thrombus formation as compared with Adamts13$^{-/-}$ mice. Thus, rA13-Plt transgenic mice exhibit a protective effect following oxidative damage.

Figure 19:
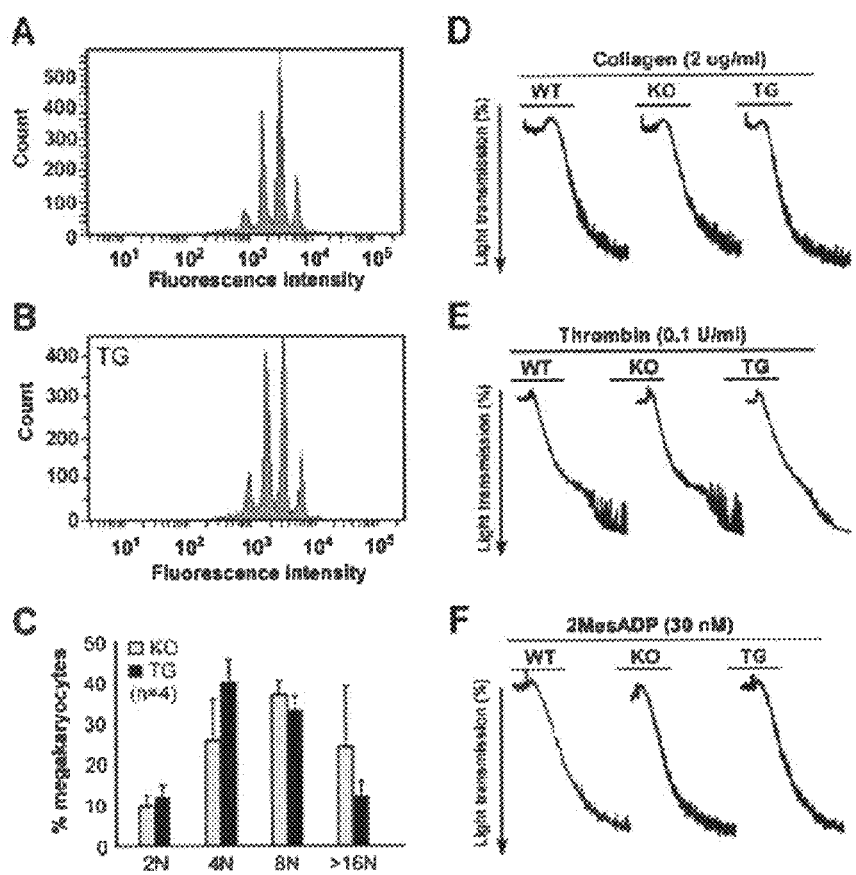
FIG. 19. Megakaryocyte maturation and platelet aggregation induced by agonists. Platelet aggregation induced by collagen, thrombin and ADP and megakaryocyte maturation in culture.

We next assessed the effect of human ADAMTS13 gene expression on megakaryocyte maturation and platelet aggregation. To examine megakaryocyte maturation, bone marrow derived megakaryocytes were isolated from knockout (FIG. 19A) and transgenic (FIG. 19B) mice in the presence of thrombopoietin and megakaryocyte ploidy was determined. No statistical differences were observed between KO and TG at various maturation stages (FIG. 19C). Platelets were isolated from Adamts13$^{-/-}$ (KO) and rA13-Plt$^{TG}$ (TG) mice, stimulated with collagen (FIG. 19D), thrombin (FIG. 19E), and 2MesADP (FIG. 19F), and platelet aggregation tracings were performed. As shown, TG mice exhibited similar ggregation as did the WT and KO platelets.

Figure 20:
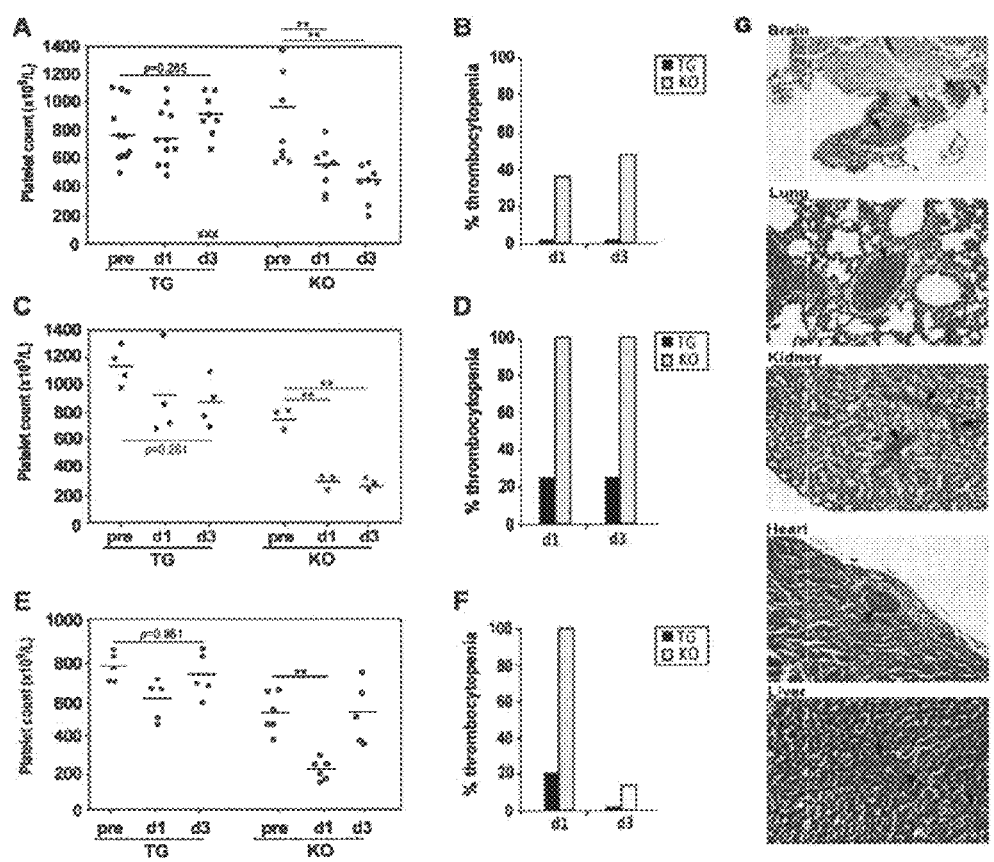
FIG. 20. STX-2 or VWF-induced TTP Syndrome. Platelet counts in mice after being challenged with Stx-2 or mVWF. Platelet counts (FIG. 20A, FIG. 20C and FIG. 20E) and the percentage of mice having thrombocytopenia (FIG. 20B, FIG. 20D, FIG. 20F) in TG and KO mice prior to (pre) 24 h (d1) and 72 h (d3) after being challenged with 20 (FIG. 20A, FIG. 20B) or 250 (FIG. 20C, FIG. 20D) picogram per gram body weight of Stx-2 or 5 microgram per gram body weight of mVWF (FIG. 20E, FIG. 20F). Histological changes in the major organs from a KO mouse that died of mVWF challenge (FIG. 20G). Arrows indicate thrombi in small arterioles. ANOVA was used to determine the statistical significance of the differences among various groups. ** indicates p value less than 0.01. Each x indicates a dead mouse. Clearly, platelet-delivered ADAMTS13 protects mice from developing either Stx2 or mVWF induced TTP as compared with Adamts13−/− mice.

To compare the susceptibility of knockout and transgenic mice toward a TTP-like syndrome, mice were challenged with shigatoxin-2 (Stx-2) or murine recombinant VWF (mVWF) (FIG. 20). Platelet counts were assessed (FIG. 20A, C, E) and the percentage of mice having thrombocytopenia (FIG. 20B, D, F) was determined. While a reduction in platelet count was observed for transgenic mice at the highest dose of Stx-2 (250 picograms per body weight) or at 5 microgram per gram body weight of mVWF, WT mice exhibited the greatest reduction under all three conditions (Figure A, C and E). Regardless of agonist dosage, transgenic mice showed a significant abrogation of percent thrombocytopenia (FIGS. 20 B, D, and F) compared to WT. Histological analysis was also performed and revealed evidence of TTP in KO mice that died from a high-dose mVWF challenge (FIG. 20G). In contrast, the majority of rA13-Plt$^{TG}$ mice were protected from challenge with shigatoxin-2 or murine recombinant VWF, which triggered a TTP-like syndrome in Adamts13$^{-/-}$ mice.

Figure 21:
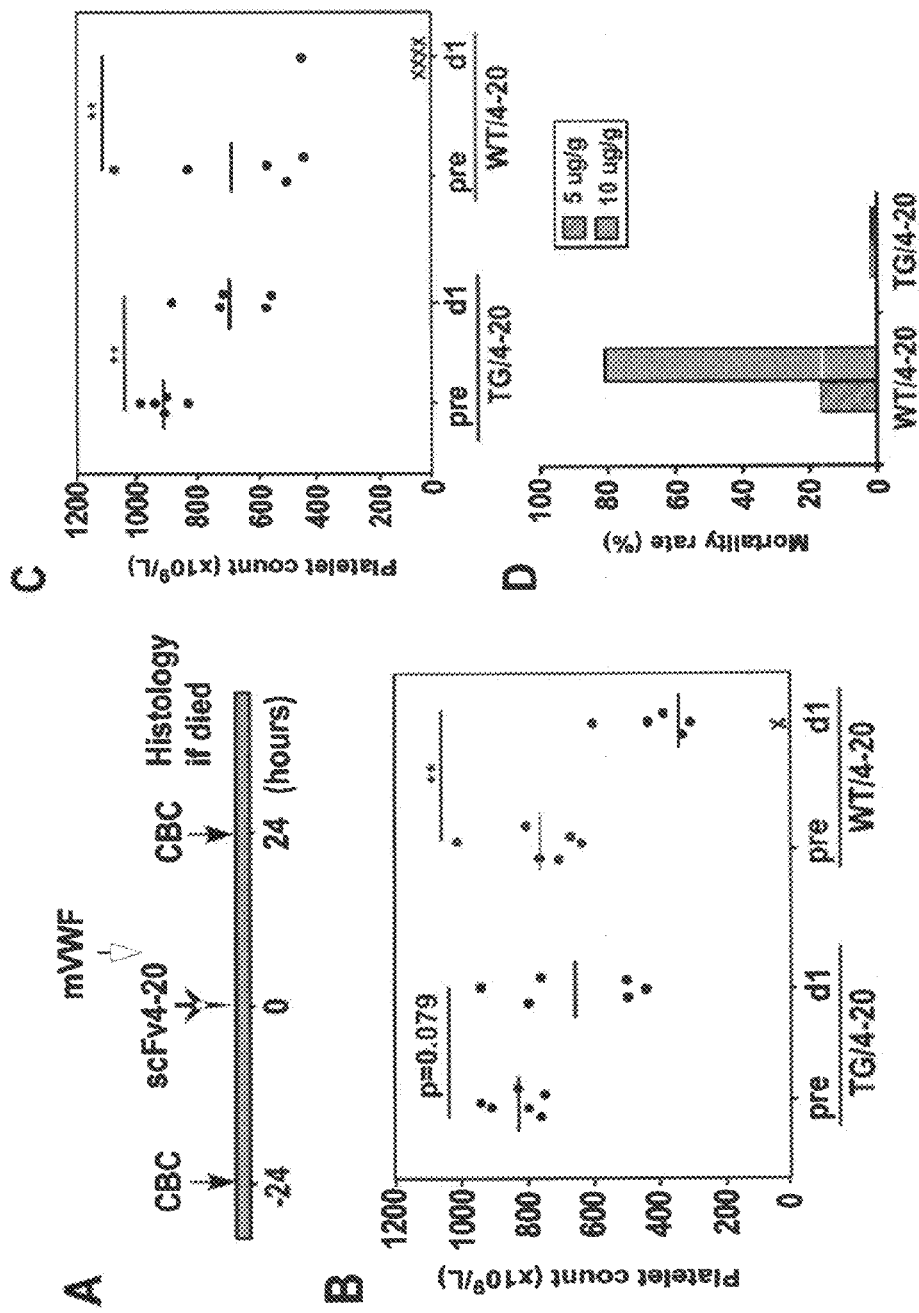
FIG. 21. Platelet-delivered ADAMTS13 protects against acquired TTP due to inhibitors. Platelet counts (CBC) and histological changes in mice with Stx or mVWF.
Figure 21:
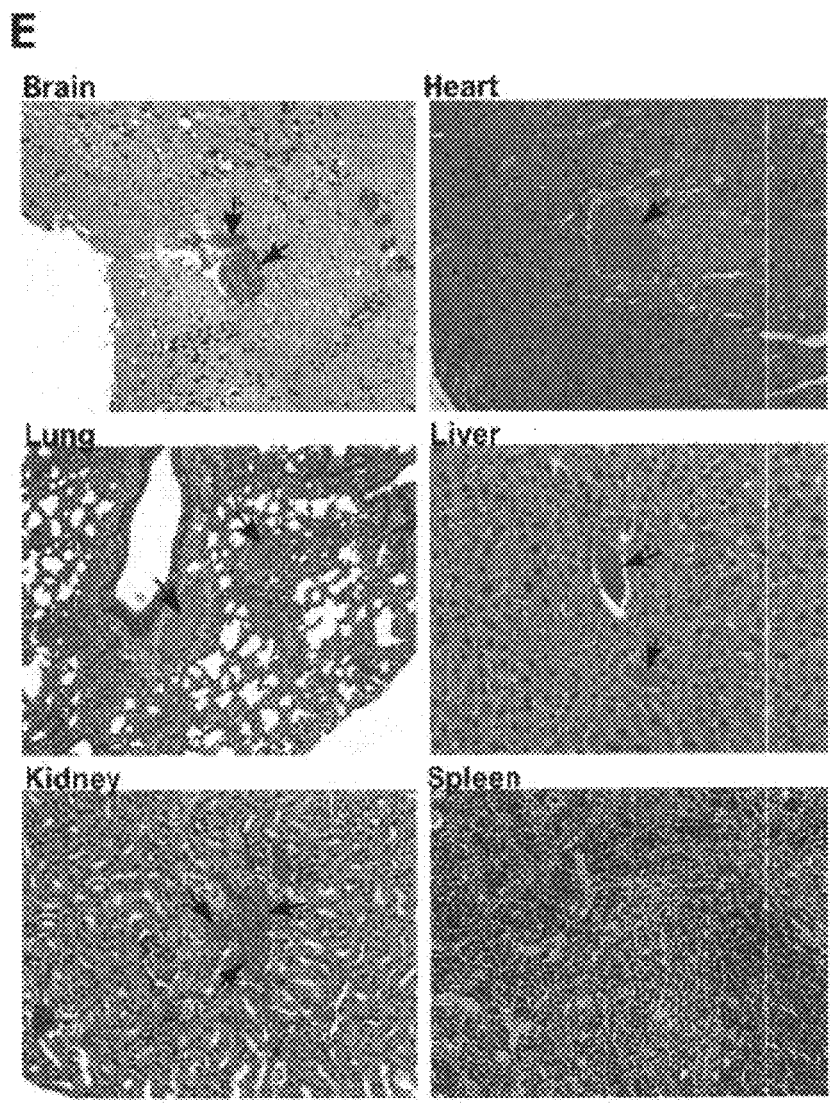

To further examine the effect of human ADAMTS13 gene expression on susceptibility toward TTP-like syndrome, platelet counts, mortality rate, and histological changes in WT or rA13-Plt$^{TG}$ mice were examined by utilizing an anti-ADAMTS13 inhibitor (scFv-20) prior to challenge with mVWF (FIG. 21) or Stx-2 (data not shown). Twenty-four hours prior to inhibitor and mVWF administration, a complete blood count (CBC) was performed; twenty-fours after administration of the mVWF and agonist, a second CBC was taken (FIG. 21A) and platelets were counted (FIG. 21B-C). Percentage of mortality was determined (FIG. 21D) and in the event of death, organs were recovered and histology was performed (FIG. 21E). While reduced platelet counts were observed in both transgenic and WT mice, the wild type mice exhibited the greatest reduction (FIGS. 21B and C) In addition, in mice administered the inhibitor and mVWF, there was a reduced mortality rate in transgenic mice compared to WT mice (FIG. 21D). Histological analysis of the major organs obtained from a WT mouse that died from VWF and inhibitor challenge revealed evidence of TTP-like syndrome (FIG. 21E). These findings indicate that in the presence or absence of an ADAMTS13 inhibitor, rA13-Plt$^{TG}$ mice are protected from induction of TTP.

Our preclinical results using transgenic mice expressing human ADAMTS13 demonstrate the efficacy of platelet-delivered ADAMTS13 in anti-arterial thrombosis and treatment of Shigatoxin-2 and VWF-induced TTP in mouse models. Therefore, we anticipate that the expression of WT and gain-of-function ADAMTS13 variants (M4 and M5) in hematopoietic progenitor cells (particularly the megakaryocytes) with in vitro transduction with a lentiviral vector encoding the genes of interest under liver-specific HAAT promoter will have significant benefit for prevention and treatment of both hereditary and acquired TTP with inhibitors, as well as other arterial thrombotic disorders. Building upon these studies, we plan on developing therapeutic strategies for use in clinical trials.

Example IV

Figure 22:
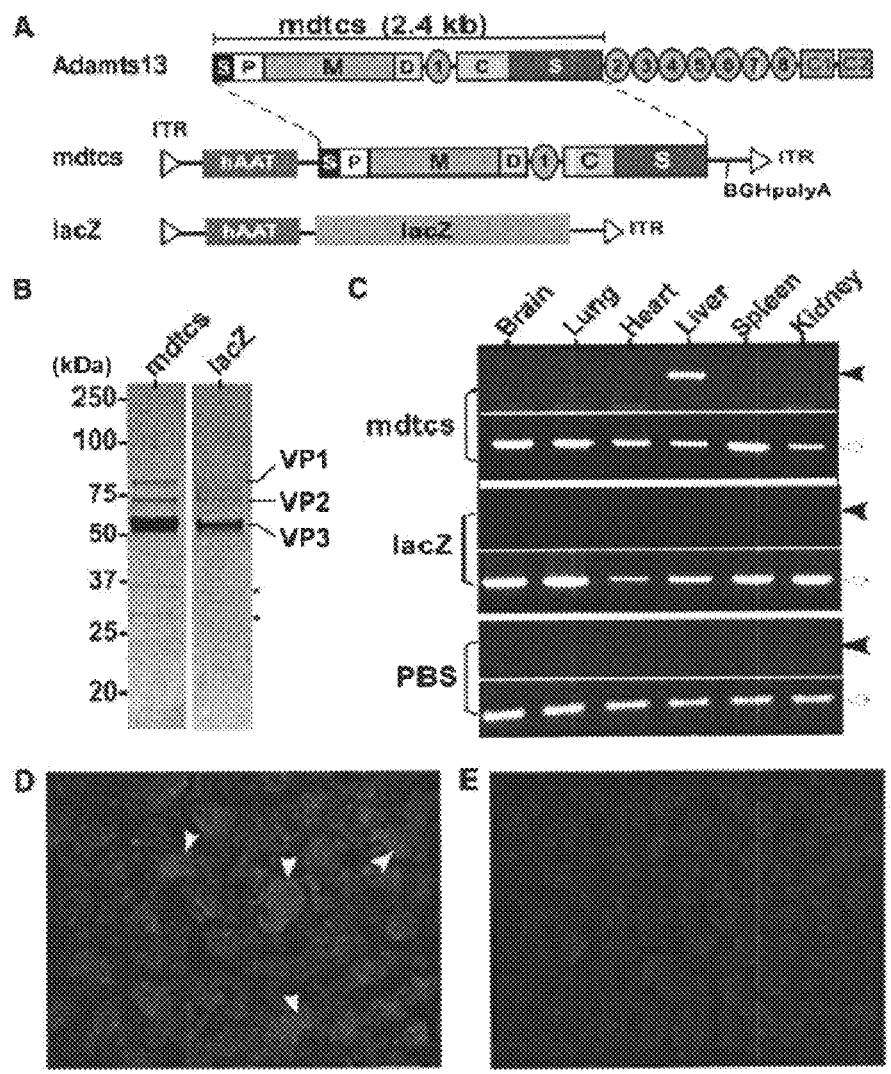
FIG. 22. Construction, preparation, and expression of AAV8 vectors.

Adeno-Associated Virus-Mediated Expression of an ADAMTS13 Variant Prevents Shigatoxin-Induced Thrombotic Thrombocytopenic Purpura To date, plasma infusion is the only effective prophylaxis or treatment available for hereditary TTP. In preclinical studies, we reported success in correction of a murine model of hereditary TTP by a single intravenous administration of an AAV8 vector encoding a C-terminal truncated murine ADAMTS13 variant (mdtcs) under the control of a liver-specific promoter (*Blood* 121:3825-3829, 2013). AAV8 vectors were produced and highly purified (FIG. 22A-B). After intravenous infusion of $2.6 \times 10^{11}$ vector genomes per kilogram (vg/kg), liver-specific expression of the transgene product was demonstrated by reverse transcriptase-polymerase chain reaction (FIG. 22C) and immunohistochemistry (FIG. 22D). Control mice that were treated with PBS or AAV8-human alpha-1 anti-trypsin (hAAT-lacZ) were negative for ADAMTS13 expression (FIG. 22C, E). Plasma ADAMTS13 activity and antigen increased with vector dosage, reaching a comparable plateau of activity (approximately 0.7 U/mL) (FIG. 23A) and antigen level (approximately 0.8 mg/mL) (FIG. 23B) after the medium to high doses. The lack of a dose response at the 2 higher doses suggests possible saturation of vector uptake and/or transgene synthetic capacity by the transduced hepatocytes.

Figure 23:
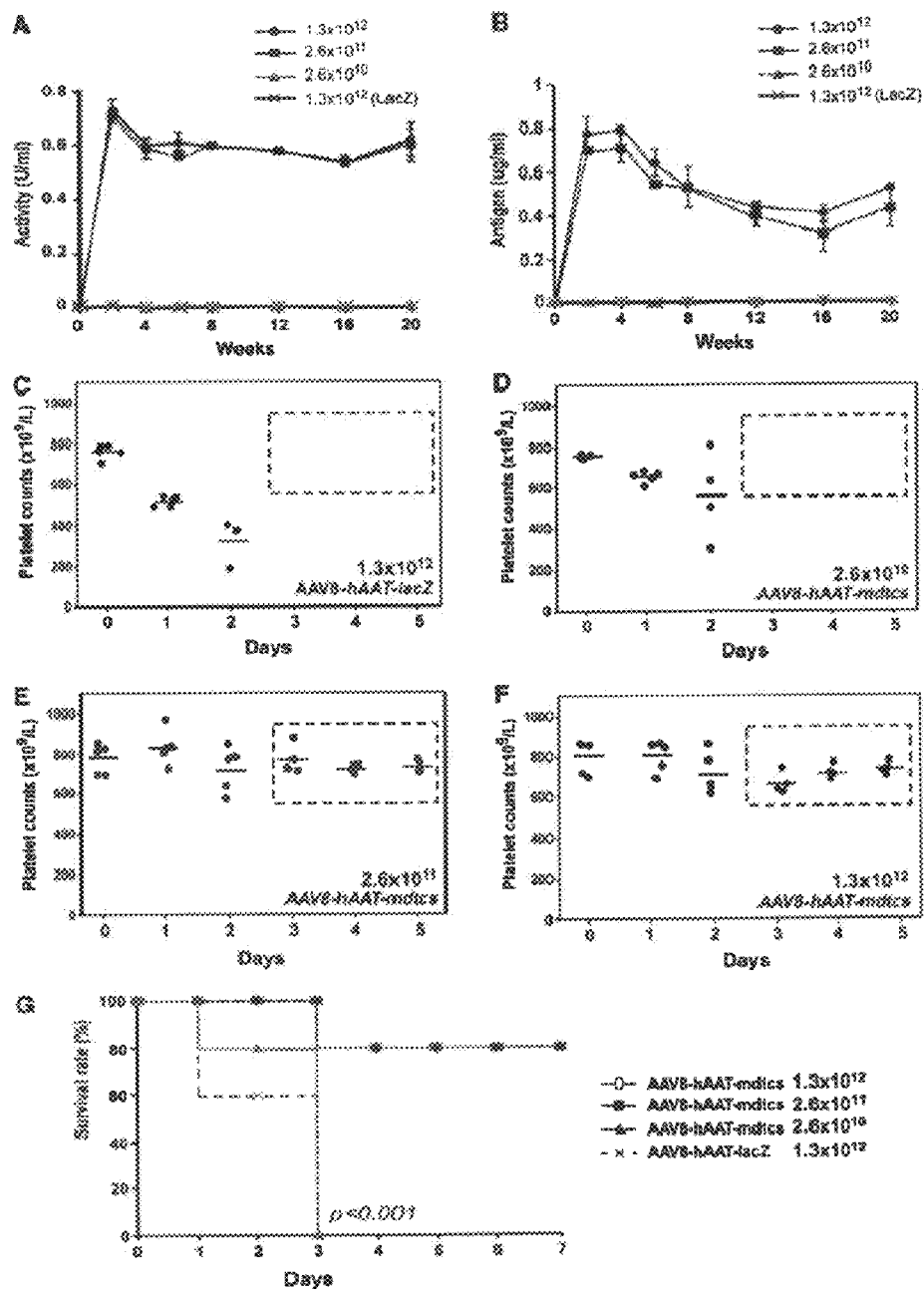
FIG. 23. Plasma levels and therapeutic efficacy of the AAV8-mediated expressed plasma ADAMTS13 variant in mice.
Figure 24:
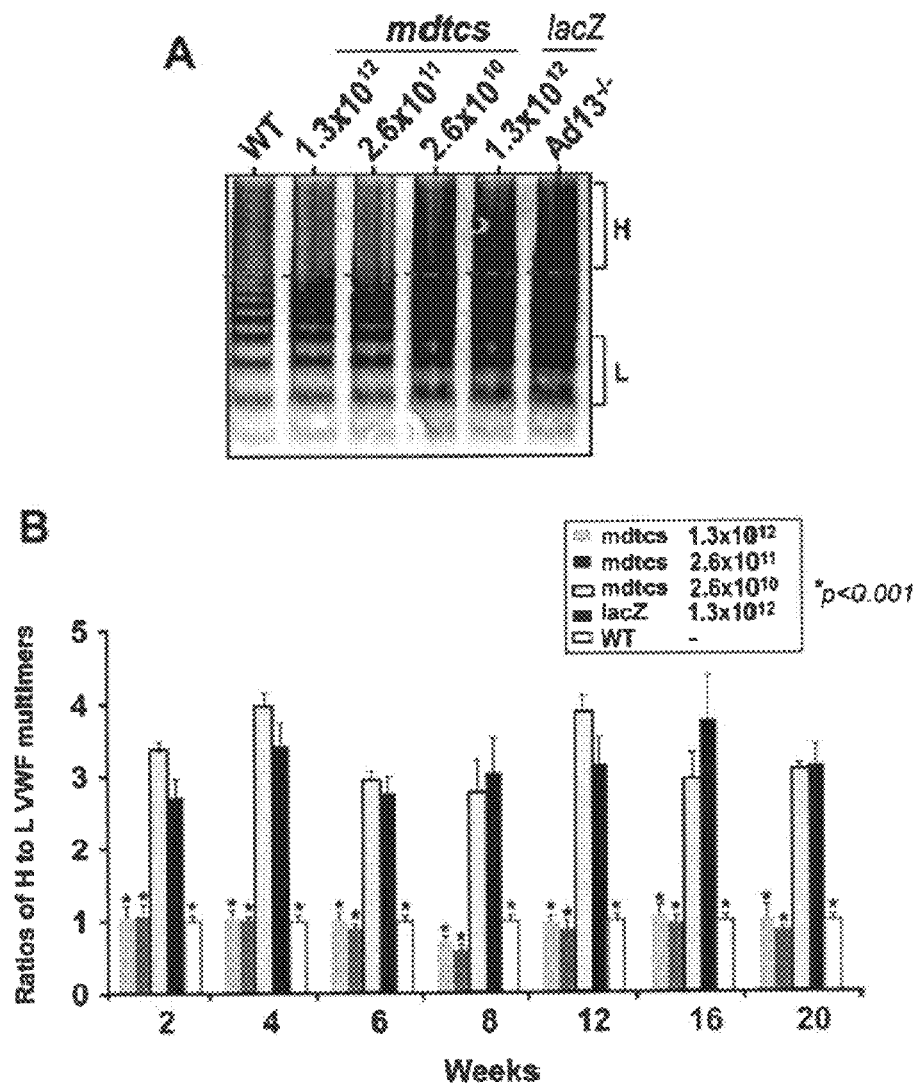
FIG. 24. Plasma VWF multimer distribution in mice treated with AAVs at various doses. Representative images of Western blotting analysis of murine plasma VWF multimers are shown for wild-type mice (WT) and Adamts13$^{-/-}$ mice 4 to 6 weeks after being treated with PBS (Ad13$^{-/-}$) or AAV8-hAAT-lacZ (lacZ) or various doses of AAV8-hAAT-mdtcs (as indicated) (FIG. 24A). The ratios of the high (H) to the low (L) molecular weight VWF multimers were quantified by densitometry using the NIH ImageJ software. The data (the means and standard deviation, n=5 in each group) from mice treated with various doses of AAV8-hAAT-mdtcs for various times after vector administration (2 to 20 weeks) are shown (FIG. 24B). The star (*) indicates the p value <0.001 as compared with that in PBS or lacZ control.

We further demonstrated that AAV8-mediated expression of a murine MDTCS fragment at vector doses greater than $2.6 \times 10^{11}$ vg/kg is sufficient to markedly reduce circulating UL-VWF or large VWF, thereby reducing ratios of high to low molecular weight multimers in plasma (FIG. 24). When challenged with Stx2, known to trigger "TTP-like" syndrome in Adamts13$^{-/-}$ CAST/Ei mice, a significant drop (40-60%) in platelet counts was observed after 24-48 hours (FIG. 23C). This severe thrombocytopenia was not detected in Adamts13$^{-/-}$ mice that received AAV8-hAAT-mdtcs at doses of 2.6×10$^{10}$ or 2.6×10$^{11}$ vg/kg (FIG. 23D,E) or 1.3× 10$^{12}$ vg/kg (FIG. 23F) 2 weeks before Stx2 challenge. All mice (5/5) in the Adamts13$^{-/-}$ cohort without vector treatment died within 32 days, but only 1 mouse (1/5) within each of the two vector-treated cohorts died (mortality rate, 20%) (p value less than 0.001) (FIG. 23G).

Figure 25:
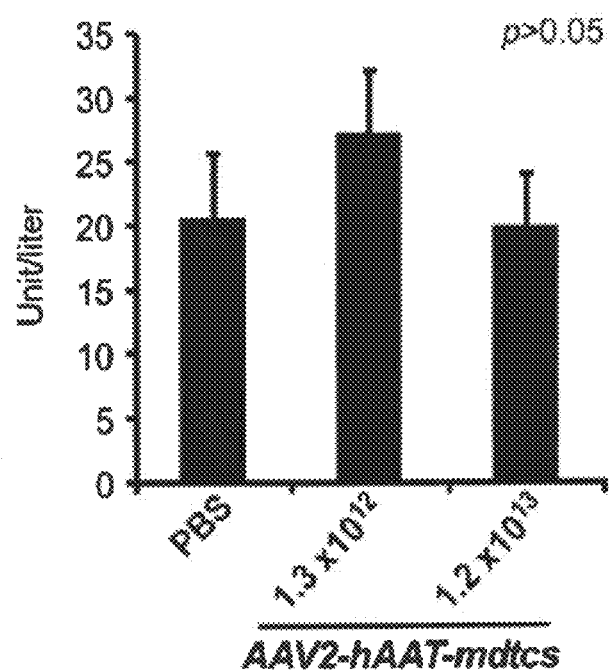
FIG. 25. Plasma alanine aminotransferase (ALT) levels in mice following AAV2 vector administration at various doses. Plasma ALT levels were determined by a colorimetric assay according to manufacturer's procedure (Teco Diagnostics, Anaheim, Calif.). Absorbance at 505 nm was obtained with the Spectrophotometer (Molecular Devices, Sunnyvale, Calif.). The data represent the means±standard error (N=5, each group). No statistically significant difference was observed among the groups, suggesting no liver toxicity with the dosage of AAV8 administration.
Figure 26:
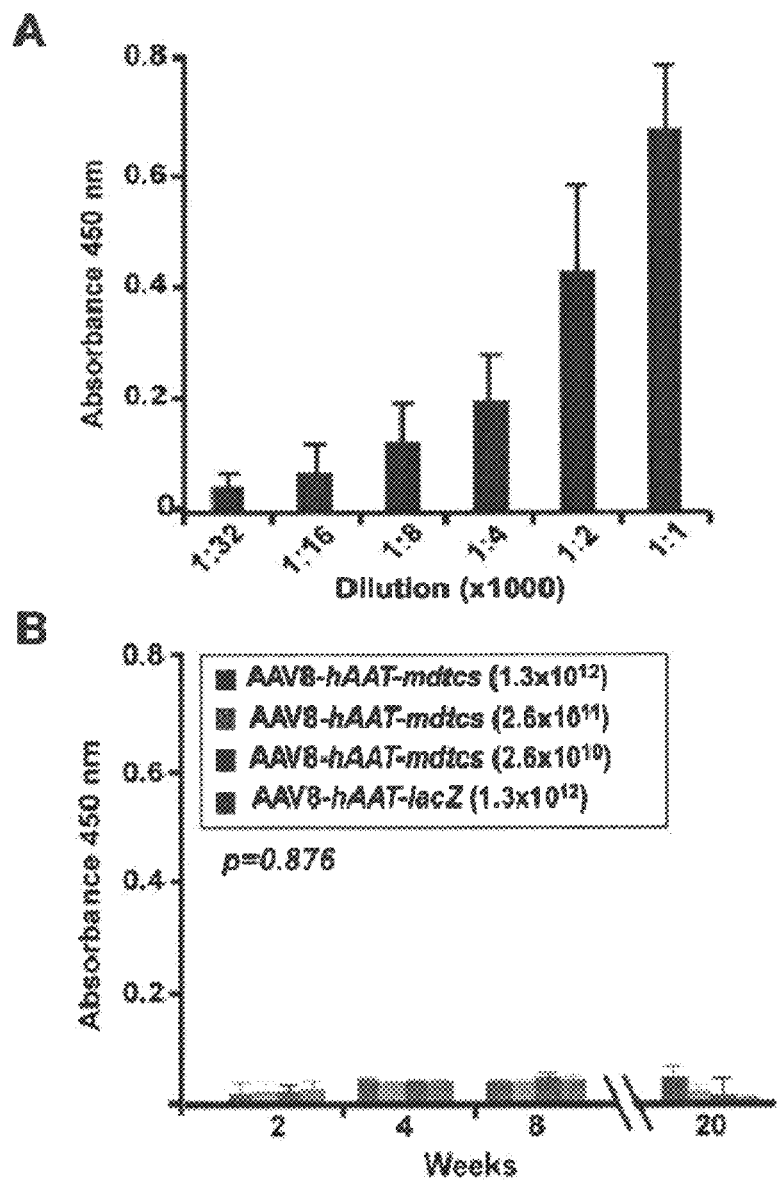
FIG. 26. Plasma anti-ADAMTS13 IgGs in AAV8-treated mice: The wells of a microtiter plate (NUNC, Rochester, N.Y.) were coated (100 μl/well) with purified recombinant mdtcs (2 μg/mL) in PBS and incubated at 25° C. for 1 hour. After blocking with 200 μl PBST containing 2.5% BSA, 100 μl of diluted murine plasma samples (1:10) or mouse anti-mdtcs serum obtained from actively immunized mice with purified mdtcs plus an adjuvant (1:1,000 to 1:32,000) (as the positive controls) were added and incubated for one hour. The wells were washed 3 times with PBST and then incubated for 1 hour with 100 μl of peroxidase-conjugated rabbit anti-mouse IgG (1:5,000) (Dako, Carpinteria, Calif.). After being washed with PBST, bound secondary antibodies were developed using TMB and quantified as described in the assay for the mdtcs antigen.

Blood smears and immunohistochemistry revealed the presence of red blood cell fragmentation and VWF-enriched microthrombi in the heart, kidneys, brain, and pancreas in Stx2-challenged Adamts13$^{-/-}$ mice pretreated with PBS or AAV8-LacZ control vector, but these pathological changes were not observed in mice pretreated with AAV8-hAAT-mdtcs or wild-type mice. Neither elevation in plasma alanine aminotransferase (FIG. 25) nor antibodies against the murine ADAMTS13 variant (FIG. 26) were detected, even at 10-fold higher vector doses.

Our preclinical results provide proof-of-concept supporting the development of an AAV based gene transfer approach for treatment of hereditary TTP in the clinic. In humans, we plan to intravenously gene transfer AAV8 or any other AAV encoding ADAMTS13-WT or gain-of-function variant (M4 or M5) at the dose of 1×10$^{11}$-1×10$^{12}$ vg/kg in patients with hereditary or acquired TTP. Approximately 50-100% of plasma ADAMTS13 activity is expected with a single dose, which lasts for at least several years or permanently. The levels of expression in plasma ADAMTS13 activity should be sufficient to correct the underlying hypercoagulable status with reduced circulating VWF multimer size and to protect against TTP episodes, triggered by infection or pregnancy.

REFERENCE LIST

1. Dong J F, Moake J L, Nolasco L et al. ADAMTS-13 rapidly cleaves newly secreted ultralarge von Willebrand factor multimers on the endothelial surface under flowing conditions. Blood 2002; 100:4033-9.
2. Tsai H M. Shear stress and von Willebrand factor in health and disease. Semin Thromb Hemost 2003; 29:479-88.
3. Vincentelli A, Susen S, Le Tourneau T et al. Acquired von Willebrand syndrome in aortic stenosis. N Engl J Med 2003; 349:343-9.
4. Banno F, Chauhan A K, Kokame K et al. The distal carboxyl-terminal domains of ADAMTS13 are required for regulation of in vivo thrombus formation. Blood 2009; 113:5323-5329.
5. Chauhan A K, Motto D G, Lamb C B et al. Systemic antithrombotic effects of ADAMTS13. J Exp Med 2006; 203:767-76.
6. Xiao J, Jin S Y, Xue J et al. Essential Domains of ADAMTS13 Metalloprotease Required for Modulation of Arterial Thrombosis. Arterioscler. Thromb. Vasc. Biol. 2011; 31:2261-2269.
7. Tsai H M. Physiologic cleavage of von Willebrand factor by a plasma protease is dependent on its conformation and requires calcium ion. Blood 1996; 87:4235-44.
8. Dong J F, Moake J L, Bernardo A et al. ADAMTS-13 metalloprotease interacts with the endothelial cell-derived ultra-large von Willebrand factor. J Biol Chem 2003; 278:29633-9.
9. Furlan M, Robles R, Lammle B. Partial purification and characterization of a protease from human plasma cleaving von Willebrand factor to fragments produced by in vivo proteolysis. Blood 1996; 87:4223-34.
10. Levy G G, Nichols W C, Lian E C et al. Mutations in a member of the ADAMTS gene family cause thrombotic thrombocytopenic purpura. Nature 2001; 413:488-94.
11. Tsai H M, Lian E C. Antibodies to von Willebrand factor-cleaving protease in acute thrombotic thrombocytopenic purpura. N Engl J Med 1998; 339:1585-94.
12. Tsai H M, Raoufi M, Zhou W et al. ADAMTS13-binding IgG are present in patients with thrombotic thrombocytopenic purpura. Thromb Haemost 2006; 95:886-92.
13. Zheng X L, Wu H M, Shang D et al. Multiple domains of ADAMTS13 are targeted by autoantibodies against ADAMTS13 in patients with acquired idiopathic thrombotic thrombocytopenic purpura. Haematologica 2010; 95:1555-1562.
14. Luken B M, Turenhout E A, Hulstein J J et al. The spacer domain of ADAMTS13 contains a major binding site for antibodies in patients with thrombotic thrombocytopenic purpura. Thromb Haemost 2005; 93:267-74.
15. Luken B M, Kaijen P H, Turenhout E A et al. Multiple B-cell clones producing antibodies directed to the spacer and disintegrin/thrombospondin type-1 repeat 1 (TSP1) of ADAMTS13 in a patient with acquired thrombotic thrombocytopenic purpura. J Thromb Haemost 2006; 4:2355-2364.
16. Luken B M, Turenhout E A, Kaijen P H et al. Amino acid regions 572-579 and 657-666 of the spacer domain of ADAMTS13 provide a common antigenic core required for binding of antibodies in patients with acquired TTP. Thromb Haemost 2006; 96:295-301.
17. Soejima K, Matsumoto M, Kokame K et al. ADAMTS-13 cysteine-rich/spacer domains are functionally essential for von Willebrand factor cleavage. Blood 2003; 102:3232-7.
18. Pos W, Crawley J T, Fijnheer R et al. An autoantibody epitope comprising residues R660, Y661, and Y665 in the ADAMTS13 spacer domain identifies a binding site for the A2 domain of VWF. Blood 2010; 115:1640-1649.
19. Pos W, Sorvillo N, Fijnheer R et al. Residues Arg568 and Phe592 contribute to an antigenic surface for anti-ADAMTS13 antibodies in the spacer domain. Haematologica 2011DOI: 10.3324/haematol.2010.036327.
20. Ai J, Smith P, Wang S, Zhang P, Zheng X L. The proximal carboxyl-terminal domains of ADAMTS13 determine substrate specificity and are all required for cleavage of von Willebrand factor. J Biol Chem 2005; 280:29428-34.
21. Gao W, Anderson P J, Majerus E M, Tuley E A, Sadler J E. Exosite interactions contribute to tension-induced cleavage of von Willebrand factor by the antithrombotic ADAMTS13 metalloprotease. Proc Natl Acad Sci USA 2006; 103:19099-04.
22. Gao W, Anderson P J, Sadler J E. Extensive contacts between ADAMTS13 exosites and von Willebrand factor domain A2 contribute to substrate specificity. Blood 2008; 112:1713-1719.
23. Zheng X L, Nishio K, Majerus E M, Sadler J E. Cleavage of von Willebrand factor requires the spacer domain of the metalloprotease ADAMTS13. J Biol Chem 2003; 278:30136-41.
24. Zhou W, Dong L, Ginsburg D, Bouhassira E E, Tsai H M. Enzymatically active ADAMTS13 variants are not inhibited by anti-ADAMTS13 autoantibodies: a novel therapeutic strategy? J Biol Chem 2005; 280:39934-39941.

25. Raife T J, Cao W, Atkinson B S et al. Leukocyte proteases cleave von Willebrand factor at or near the ADAMTS13 cleavage site. Blood 2009; 114:1666-74.
26. Zhang L, Lawson H L, Harish V C et al. Creation of a recombinant peptide substrate for fluorescence resonance energy transfer-based protease assays. Anal. Biochem. 2006; 358:298-300.
27. Cao W J, Krishnaswamy S, Camire R M, Lenting P J, Zheng X L. Factor VIII accelerates proteolytic cleavage of von Willebrand factor by ADAMTS13. Proc Natl Acad Sci USA 2008; 105:7416-21.
28. Jin S Y, Skipwith C G, Zheng X L. Amino acid residues Arg(659), Arg(660), and Tyr(661) in the spacer domain of ADAMTS13 are critical for cleavage of von Willebrand factor. Blood 2010; 115:2300-2310.
29. Akiyama M, Takeda S, Kokame K, Takagi J, Miyata T. Crystal structures of the noncatalytic domains of ADAMTS13 reveal multiple discontinuous exosites for von Willebrand factor. Proc Natl Acad Sci USA 2009; 106:19274-19279.
30. Zhang Q, Zhou Y F, Zhang C Z et al. Structural specializations of A2, a force-sensing domain in the ultralarge vascular protein von Willebrand factor. Proc. Natl. Acad. Sci. U.S.A 2009; 106:9226-9231.
31. Klaus C, Plaimauer B, Studt J D et al. Epitope mapping of ADAMTS13 autoantibodies in acquired thrombotic thrombocytopenic purpura. Blood 2004; 103:4514-9.
32. George J N. How I treat patients with thrombotic thrombocytopenic purpura: 2010. Blood 2010; 116:4060-4069.
33. Zheng X L, Richard K M, Goodnough L T, Sadler J E. Effect of plasma exchange on plasma ADAMTS13 metalloprotease activity, inhibitor level, and clinical outcome in patients with idiopathic and non-idiopathic thrombotic thrombocytopenic purpura. Blood 2004; 103:4043-9.
34. Zheng X L, Sadler J E. Pathogenesis of Thrombotic Microangiopathies. Annu. Rev. Path. Mech. Dis. 2008; 3:249-277.
35. Cataland S R, Jin M, Zheng X L, George J N, Wu H M. An evaluation of cyclosporine alone for the treatment of early recurrences of thombotic thrombocytopenic purpura. J Thromb Haemost 2006; 4:1162-4.
36. Cataland S R, Jin M, Lin S et al. Cyclosporin and plasma exchange in thrombotic thrombocytopenic purpura: long-term follow-up with serial analysis of ADAMTS13 activity. Br J Haematol 2007; 139:486-93.
37. Fakhouri F, Teixeira L, Delarue R, Grunfeld J P, Veyradier A. Responsiveness of thrombotic thrombocytopenic purpura to rituximab and cyclophosphamide. Ann Intern Med 2004; 140:314-5.
38. Zheng X L, Pallera A M, Goodnough L T, Sadler J E, Blinder M A. Remission of chronic thrombotic thrombocytopenic purpura after treatment with cyclophosphamide and rituximab. Ann. Intern. Med. 2003; 138:105-108.
39. Shelat S G, Smith A G, Ai J, Zheng X. L. Inhibitory autoantibodies against ADAMTS-13 in patients with thrombotic thrombocytopenic purpura bind ADAMTS-13 protease and may accelerate its clearance in vivo. J Thromb Haemost 2006; 4:1707-17.
40. Jin, S., Xia, J., Bao, J., Zhou, S., Wright, J. F., Zheng, X. L. AAV-mediated expression of an ADAMTS13 variant prevents shigatoxin-induced thrombotic thrombocytopenic purpura. Blood 2013; 121:3825-3829.

While the invention has been described in detail and with reference to specific examples thereof, it will be apparent to one skilled in the art that various changes and modifications can be made therein without departing from the spirit and scope thereof.

What is claimed is:

1. An isolated, recombinantly produced gain-of-function a disintegrin and metalloprotease with thromboppondin type 1 repeats-13 (ADAMTS13) human variant protein comprising at least one amino acid change in a spacer domain of the full-length ADAMTS13 comprising amino acids 1-2050, said variant having increased proteolytic activity of multimeric von Willebrand factor (VWF) and exhibiting resistance to anti-ADAMTS13 autoantibody inhibition relative to wild type the human ADAMTS13 lacking said at least one amino acid change, wherein said variant is selected from the group consisting of:
   i) an M4 variant, wherein an arginine at position 660 is replaced with a lysine, a phenylalanine at position 592 is replaced with a tyrosine, an arginine at position 568 is replaced with a lysine and an arginine at position 661 is replaced with a phenylalanine; and
   ii) an M5 variant, wherein an arginine at position 660 is replaced with a lysine, a phenylalanine at position 592 is replaced with a tyrosine, an arginine at position 568 is replaced with a lysine, an arginine at position 661 is replaced with a phenylalanine and a tyrosine at position 665 is replaced with a phenylalanine.

2. The isolated, recombinantly produced ADAMTS13 variant of claim 1 which is the M4 variant.

3. A pharmaceutical composition comprising the isolated ADAMTS13 variant of claim 1, in a biologically acceptable carrier.

* * * * *

UNITED STATES PATENT AND TRADEMARK OFFICE
CERTIFICATE OF CORRECTION

PATENT NO. : 9,546,360 B2
APPLICATION NO. : 14/312041
DATED : January 17, 2017
INVENTOR(S) : X. Long Zheng Page 1 of 1

It is certified that error appears in the above-identified patent and that said Letters Patent is hereby corrected as shown below:

At Column 1, Lines 12-15:
Please delete:
"Pursuant to 35 U.S.C. §202(c) it is acknowledged that the U.S. Government has rights in the invention described, which was made in part with funds from the National Institutes of Health, Grant Number, HL074124."
And insert therefor:
--This invention was made with government support under grant number HL074124 awarded by the National Institutes of Health. The government has certain rights in the invention.--

Signed and Sealed this
Tenth Day of March, 2020

Andrei Iancu
*Director of the United States Patent and Trademark Office*